US009540612B2

(12) United States Patent
Lemischka et al.

(10) Patent No.: US 9,540,612 B2
(45) Date of Patent: Jan. 10, 2017

(54) METHODS FOR PROGRAMMING DIFFERENTIATED CELLS INTO HEMATOPOIETIC STEM CELLS

(71) Applicant: Icahn School of Medicine at Mount Sinai, New York, NY (US)

(72) Inventors: Ihor R. Lemischka, Princeton, NJ (US); Kateri Moore, Princeton, NJ (US); Carlos Filipe Pereira, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/374,639

(22) PCT Filed: Jan. 30, 2013

(86) PCT No.: PCT/US2013/023803
§ 371 (c)(1),
(2) Date: Jul. 25, 2014

(87) PCT Pub. No.: WO2013/116307
PCT Pub. Date: Aug. 8, 2013

(65) Prior Publication Data
US 2015/0004145 A1  Jan. 1, 2015

Related U.S. Application Data

(60) Provisional application No. 61/592,238, filed on Jan. 30, 2012.

(51) Int. Cl.
*C12N 5/0789* (2010.01)
*G01N 33/483* (2006.01)
*G01N 33/50* (2006.01)
*A61K 35/00* (2006.01)

(52) U.S. Cl.
CPC ......... *C12N 5/0647* (2013.01); *G01N 33/5014* (2013.01); *A61K 35/00* (2013.01); *C12N 2501/60* (2013.01); *C12N 2501/998* (2013.01); *C12N 2502/1394* (2013.01); *C12N 2506/13* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,004,681 | A | 4/1991 | Boyse et al. |
| 5,192,553 | A | 3/1993 | Boyse et al. |
| 5,656,498 | A | 8/1997 | Iijima et al. |
| 5,955,257 | A | 9/1999 | Burger et al. |
| 6,461,645 | B1 | 10/2002 | Boyse et al. |
| 2003/0215942 | A1 | 11/2003 | Chow et al. |
| 2004/0029188 | A1 | 2/2004 | Eaves et al. |
| 2006/0292695 | A1 | 12/2006 | Clark et al. |
| 2008/0248503 | A1 | 10/2008 | Rich |
| 2011/0008823 | A1 | 1/2011 | McKim |
| 2012/0214236 | A1 | 8/2012 | Bhatia et al. |
| 2012/0301438 | A1 | 11/2012 | Cheng |
| 2014/0037600 | A1* | 2/2014 | Yu et al. ............. 424/93.21 |

FOREIGN PATENT DOCUMENTS

WO  WO-2010/117879 A1  10/2010

OTHER PUBLICATIONS

Sandler et al., Reprogramming of Embryonic Human Fibroblasts into Fetal Hematopoietic Progenitors by Fusion with Human Fetal Liver CD34+ Cells. PloS ONE 2011, 6: e18265 p. 1-9.*
Minegishi et al., Expression and domain-specific function of GATA-2 during differentiation of the hematopoietic precursor cells in midgestation mouse embryos. Blood, Aug. 1, 2003 vol. 102, p. 896-905.*
Saleque et al., The zinc-finger proto-oncogene Gfi-Ib is essential for development of the erythroid and megakaryocytic lineages. Genes & Development 16:301-306, 2002.*
Okada et al., Prolonged Expression of c-fos Suppresses Cell Cycle Entry of Dormant Hematopoietic Stem Cells. Blood, vol. 93, No. 3 Feb. 1, 1999: pp. 816-825.*
Calvanese et al., 4314 Analysis of Highly Self-Renewing GPI-80+ Human Fetal Hematopoietic Stem Cells Identifies Novel Regulators of Stemness. 56th American Society of Hematology Meeting. Dec. 2014, p. 1.*
Vodyanik et al., Leukosialin (CD43) defines hematopoietic progenitors in human embryonic stem cell differentiation cultures. 2006; Blood: 108 (6): 2095-2105.*
Ang et al., Wdr5 mediates self-renewal and reprogramming via the embryonic stem cell core transcriptional network. *Cell* 145: 183-97 (2011).
Batzer et al., Enhanced evolutionary PCR using oligonucleotides with inosine at the 3'-terminus. *Nucl. Acid Res.* 19: 5081 (1991).
Brunet et al., Metagenes and molecular pattern discovery using matrix factorization. *Proc. Natl. Acad. Sci. USA* 101: 4164-9 (2004).
Carvajal-Vergara et al., Patient-specific induced pluripotent stem-cell-derived models of LEOPARD syndrome. *Nature* 465: 808-12 (2010).
Chu et al., SV40 DNA transfection of cells in suspension: analysis of efficiency of transcription and translation of T-antigen. *Gene* 13:197-202 (1981).
Ciau-Uitz et al., Tel1/ETV6 specifies blood stem cells through the agency of VEGF signaling. *Develop. Cell*, 18(4): 569-87 (2010).
Clark et al., Introduction to statistical methods to analyze large data sets: principal components analysis. *Sci. Signal* 4(190):tr3 (2011).

(Continued)

*Primary Examiner* — Christopher M Babic
*Assistant Examiner* — Arthur S Leonard
(74) *Attorney, Agent, or Firm* — Marshall, Gerstein & Borun LLP

(57) ABSTRACT

The disclosure relates to the development of methods for making hematopoietic stem cells from differentiated cells by introducing and expressing transcription factors. More particularly, the disclosure provides methods for redirecting differentiated cells to a hematopoietic stem cell state or to a hemogenic endothelial cell state by direct programming with specific combinations of transcription factors.

22 Claims, No Drawings

(56) References Cited

OTHER PUBLICATIONS

Deneault et al., A functional screen to identify novel effectors of hematopoietic stem cell activity. *Cell* 137: 369-79 (2009).
Feng et al., PU.1 and C/EBPalpha/beta convert fibroblasts into macrophage-like cells. *Proc. Natl. Acad. Sci. USA* 105: 6057-62 (2008).
Graham et al., A new technique for the assay of infectivity of human adenovirus 5 DNA. *Virology* 52:456-67 (1973).
Hanna et al., Pluripotency and cellular reprogramming: facts, hypotheses, unresolved issues. *Cell* 143: 508-25 (2010).
Huang et al., Induction of functional hepatocyte-like cells from mouse fibroblasts by defined factors. *Nature* 475: 386-91 (2011).
Ieda et al., Direct reprogramming of fibroblasts into functional cardiomyocytes by defined factors. *Cell* 142: 375-86 (2010).
Irion et al., Temporal specification of blood progenitors from mouse embryonic stem cells and induced pluripotent stem cells. *Development* 137: 2829-39 (2010).
Kent et al., The human genome browser at UCSC. *Genome Res.* 12: 996-1006 (2002).
Khandanpour et al., Evidence that growth factor independence 1b regulates dormancy and peripheral blood mobilization of hematopoietic stem cells. *Blood* 116(24): 5149-61 (2010).
Kinoshita et al., Host control of HIV-1 parasitism in T cells by the nuclear factor of activated T cells. *Cell* 95: 595-604 (1998).
Kumagai et al., Use of stroma-supported cultures of leukemic cells to assess antileukemic drugs. II. Potent cytotoxicity of 2-chlorodeoxyadenosine in acute lymphoblastic leukemia. *Leukemia* 8: 1116-23 (1994).
Lancrin et al., GFI1 and GFI1B control the loss of endothelial identity of hemogenic endothelium during hematopoietic commitment. *Blood* 120: 314-22 (2012).
Langmead et al., Ultrafast and memory-efficient alignment of short DNA sequences to the human genome. *Genome Biol.* 10(3): R25 (2009).
Li et al., The Sequence Alignment/Map format and SAMtools. *Bioinformatics* 25: 2078-9 (2009).
Moore et al., In vitro maintenance of highly purified, transplantable hematopoietic stem cells. *Blood* 89: 4337-47 (1997).
Nolta et al., The AFT024 stromal cell line supports long-term ex vivo maintenance of engrafting multipotent human hematopoietic progenitors. *Leukemia* 16: 352-61 (2002).
Ohtsuka et al., An alternative approach to deoxyoligonucleotides as hybridization probes by insertion of deoxyinosine at ambiguous codon positions. *J. Biol. Chem.* 260: 2605-8 (1985).
Okada et al., Prolonged expression of c-fos suppresses cell cycle entry of dormant hematopoietic stem cells. *Blood* 93(3): 816-25 (1999).
Quinlan et al., BEDTools: a flexible suite of utilities for comparing genomic features. *Bioinformatics* 26: 841-2 (2010).
Radomska et al., Transgenic targeting with regulatory elements of the human CD34 gene. *Blood* 100: 4410-19 (2002).
Reich et al., GenePattern 2.0. *Nat. Genet.* 38: 500-1 (2006).
Roberts et al., Improving RNA-Seq expression estimates by correcting for fragment bias. *Genome Biol.* 12: R22 (2011).
Robinson et al., Integrative genomics viewer. *Nat. Biotechnol.* 29: 24-6 (2011).
Rossolini et al., Use of deoxyinosine-containing primers vs degenerate primers for polymerase chain reaction based on ambiguous sequence information. *Mol. Cell. Probes* 8: 91-8 (1994).
Schaniel et al., Genetic models to study quiescent stem cells and their niches. *Ann. N.Y. Acad. Sci.* 1176: 26-35 (2009).
Sommer et al., Excision of reprogramming transgenes improves the differentiation potential of iPS cells generated with a single excisable vector. *Stem Cells* 28:64-7 (2010).
Spurgeon et al., High throughput gene expression measurement with real time PCR in a microfluidic dynamic array. *PLoS One* 3(2): e1662 (2008).
Subramanian et al., Gene set enrichment analysis: a knowledge-based approach for interpreting genome-wide expression profiles. *Proc. Natl. Acad. Sci. USA* 102: 15545-50 (2005).
Szabo et al, Direct conversion of human fibroblasts to multilineage blood progenitors. *Nature* 468: 521-6 (2010).
Takahashi et al., Induction of pluripotent stem cells from adult human fibroblasts by defined factors. *Cell* 131: 861-72 (2007).
Takahashi et al., Induction of pluripotent stem cells from mouse embryonic and adult fibroblast cultures by defined factors. *Cell*, 126: 663-76 (2006).
Trapnell et al., Differential gene and transcript expression analysis of RNA-seq experiments with TopHat and Cufflinks. *Nat. Protoc.* 7: 562-78 (2012).
Trapnell et al., TopHat: discovering splice junctions with RNA-Seq. *Bioinformatics* 25: 1105-11 (2009).
Trapnell et al., Transcript assembly and quantification by RNA-Seq reveals unannotated transcripts and isoform switching during cell differentiation. *Nat. Biotechnol.* 28: 511-5 (2010).
Tsai et al., Single transcription factor reprogramming of hair follicle dermal papilla cells to induced pluripotent stem cells. *Stem Cells* 29: 964-71 (2011).
Tumbar et al., Defining the epithelial stem cell niche in skin. *Science* 303: 359-63 (2004).
Van Den Heuvel et al., Use of in vitro assays to assess hematotoxic effects of environmental compounds. *Cell Biol. Toxicol.* 17: 107-16 (2001).
Vierbuchen et al., Direct conversion of fibroblasts to functional neurons by defined factors. *Nature*, 463: 1035-41 (2010).
Vierbuchen et al., Direct lineage conversions: unnatural but useful? *Nat. Biotechnol.* 29: 892-907 (2011).
Warren et al., Highly efficient reprogramming to pluripotency and directed differentiation of human cells with synthetic modified mRNA. *Cell Stem Cell* 7(5): 618-30 (2010).
Wilson et al., Combinatorial transcriptional control in blood stem/progenitor cells: genome-wide analysis of ten major transcriptional regulators. *Cell Stem Cell* 7: 532-44 (2010).
Xie et al., Stepwise reprogramming of B cells into macrophages. *Cell* 117: 663-76 (2004).
Zhou et al., In vivo reprogramming of adult pancreatic exocrine cells to beta-cells. *Nature* 455: 627-32 (2008).

\* cited by examiner

METHODS FOR PROGRAMMING DIFFERENTIATED CELLS INTO HEMATOPOIETIC STEM CELLS

CROSS REFERENCE TO RELATED APPLICATIONS

The present application claims the benefit of priority to U.S. Provisional Application No. 61/592,238, filed Jan. 30, 2012. The disclosure of the priority application is incorporated herein by reference in its entirety.

INCORPORATION BY REFERENCE OF MATERIAL SUBMITTED ELECTRONICALLY

This application contains as a separate part of disclosure a Sequence Listing in computer-readable form (filename: 45924A_SeqListing.txt; created Jan. 30, 2013, 44,553 bytes—ASCII text file) which is incorporated by reference in its entirety.

FIELD

The disclosure generally relates to methods for regenerative medicine and methods for developing stem cells. More particularly, the disclosure provides methods for redirecting differentiated cells to a self-renewing hematopoietic stem cell state by direct programming with transcription factors.

BACKGROUND

Bone marrow (BM) transplantation was the first and continues to be the most successful example of a stem cell-based therapy. Nevertheless, there remains a constant, critical shortage of stem cells to meet the needs of patients suffering from hematological or other diseases requiring BM transplantation. This shortage is due to a lack of sufficient numbers of immunologically compatible donors and the limited numbers of hematopoietic stem cells (HSCs) contained within a donor product, especially in umbilical cord blood transplantation.

HSC transplantation (HSCT) was the first successful example of a stem cell-based treatment. The systematic application of HSCT, however, has been limited by the availability of matching donors, by administration of immunosuppressive drugs to prevent transplant rejection, and by the limited HSC number/availability.

Direct programming of HSCs from reprogramming differentiated cells, whether from the individual patient or a suitable donor, offers an exciting alternative to overcome these limitations. This reprogramming of differentiated cells to HSCs also avoids ethical issues associated with the use of HSCs derived from embryonic stem cells (ESCs) and circumvents complete induced pluripotent stem cell (iPSC) reprogramming to pluripotency with subsequent directed differentiation to hematopoietic cells. Indeed, the directed differentiation of either ESCs or iPSCs to bona fide HSCs remains elusive. Direct programming of HSCs could provide a universal and unlimited source material for cell replacement therapy of hematological diseases.

Reprogramming cell identity holds great promise for biomedicine as a major source of patient-specific cell-types for transplantation-based therapies. While reprogramming was achieved towards pluripotent and some differentiated cell fates, the direct programming of multipotent adult stem cells, such as HSCs remain to be accomplished.

HSCs continuously replenish all blood cell lineages. Their hallmark property is the ability to strike a balance between self-renewal and differentiation to form mature blood. The transcriptional regulatory network of HSCs is just starting to be addressed on a global scale. Genome-wide binding maps of transcription regulators and gain-of-function screening approaches recently have provided global insight on the combinatorial transcriptional control of HSCs (Wilson et al., Cell Stem Cell 7:532-44, 2010; Deneault et al., Cell 137: 369-79, 2009). Seminal experiments by Yamanaka and colleagues showed that retroviral-mediated expression of Oct4, Sox2, c-Myc and Klf4 could drive mouse and human fibroblasts into an iPSC state (Takahashi et al., Cell 126: 663-76, 2006; Takahashi et al., Cell 131: 861-72, 2007). These pioneering studies have illustrated the importance of a limited combination of transcription factors for the induction of pluripotency. Later studies have shown that certain factors could be replaced with small molecules and the direct conversion towards other cell identities (Hanna et al., Cell 143: 508-25, 2010). In this way, for example, the transcription factors C/EBPα/β and PU.1 were found to induce a macrophage fate in lymphoid cells and fibroblasts (Xie et al., Cell 117: 663-76, 2004; Feng et al., Proc. Natl. Acad. Sci. USA 105: 6057-62, 2008); Ascl1, Brn2/Pou3f2 and Mytl1 to induce neuronal identity in fibroblasts (Vierbuchen et al., Nature 463:1035-41, 2010); Gata4, Mef2c and Tbx5 to induce fibroblasts to cardiomyocytes (Leda et al., Cell 142: 375-86, 2010); Ngn3, Pdx1, and Mafa reprogram pancreatic exocrine cells to beta cells (Zhou et al., Nature 425:627-632, 2008); and Gata4, Hnf1a and FoxA3 induce hepatocyte-like cells from mouse fibroblasts (Huang et al., Nature 475:386-391, 2011). In addition, it recently was reported that overexpression of Oct4 together with specific cytokine treatment can direct fibroblasts to a myeloid/ erythroid progenitor cell fate (Szabo et al, Nature 468: 521-6, 2010). It is unclear, however, if Oct4 acts by inducing de-differentiation or by mimicking the action of the family member Oct1 which is expressed in hematopoietic tissues. The hematopoietic progenitors generated do not retain self-renewal and the same degree of multipotency as HSCs, e.g., hematopoietic progenitors do not give rise to lymphoid cells.

Collectively, these direct reprogramming results raise the question of whether there is a particular transcription factor signature that can be used for programming adult somatic stem cells that self-renew and are able to differentiate in all lineages of the hemato-lymphoid system. To date, direct programming of differentiated cells to bona fide HSCs or primitive hematopoietic progenitors has not been demonstrated.

Thus, the art to date does not disclose methods for the direct programming of HSCs. Accordingly, a strong need in the art exists for a method of programming differentiated cells into HSCs. The following disclosure describes the specifics of such a method.

SUMMARY

The methods described herein were developed to provide a means for the direct programming of HSCs from differentiated cells. More specifically, the disclosure provides methods for direct programming of HSCs from differentiated cells, such that differentiated cells, e.g., cells derived from endoderm, mesoderm, and/or ectoderm, are programmed or transformed into cells of a self-renewing HSC state by introducing and expressing key transcription factors in the differentiated cells.

The disclosure provides a method for programming a differentiated cell into a hematopoietic stem cell, the method comprising introducing a combination of transcription factors in the differentiated cell, wherein the combination comprises GATA binding protein 2 (GATA2), growth factor independent 1B (GFI1B), and c-Fos. In some aspects, the combination of transcription factors further comprises ETS translocation variant 6 (ETV6). In additional aspects, the combination of transcription factors further comprises one or more transcription factors selected from the group consisting of stem cell leukemia (SCL/TAL1), runt-related transcription factor 1 (RUNX1), and B lymphoma Mo-MLV insertion region 1 homolog (BMI1). In another aspect, such methods further comprise the step of screening the cell for expression of a hemogenic endothelial cell marker or a hematopoietic stem cell marker or for uptake of acetylated low density lipoprotein. In some aspects, the hemogenic endothelial cell marker or the hematopoietic stem cell marker is a marker selected from the group consisting of: CD31, CD34, CD38$^{lo/-}$, CD41, CD43, CD45, CD49f, Thy1/CD90, CD105, CD117/c-kit, CD133, CD150, Sca-1, Tie2, VE-Cadherin, KDR/FLK1, Flk-2/Flt3, and CXCR4. In more particular aspects, the hematopoietic stem cell marker is selected from the group consisting of: CD31, CD34, CD41, CD117/c-kit, CD133, Sca-1, Tie2, VE-Cadherin, and CD150. In some aspects, the methods of the disclosure further comprise the step of screening the cell for a lack of expression of a differentiated hematopoietic lineage (lin) marker, i.e., screening for a lin$^-$ cell. In such aspects, the lin– marker is selected from the group consisting of CD4, CD5, CD8, CD45RA/B220, Gr-1/Ly-6G/C, and Ter119.

The methods of the disclosure, in some aspects, further comprise the step of isolating the cell expressing the hematopoietic stem cell marker. In some aspects, such methods also further comprise the step of co-culturing the hematopoietic stem cell with other cells. In some aspects, the other cells are stromal cells. Such stromal cells, in some aspects, include AFT024 stromal cells.

The disclosure also includes isolated HSCs obtained by any of the methods described herein. The disclosure further includes a composition comprising such isolated HSCs and an appropriate vehicle for delivery of the cells to a subject in need thereof. In addition, the disclosure includes a composition comprising such isolated HSCs and a cryoprotectant.

The disclosure also includes a method for treating a subject who suffers from a condition or a disease that would benefit from hematopoietic stem cell transplantation. In some aspects, the condition or disease is a type of cancer, a congenital disorder, or a type of vascular disease. In more particular aspects, the condition or disease is selected from the group consisting of multiple myeloma, leukemia, congenital neutropenia with defective stem cells, aplastic anemia, myelodysplastic syndrome, neuroblastoma, lymphoma, Ewing's Sarcoma, Desmoplastic small round cell tumor, chronic granulomatous disease, non-Hodgkin's lymphoma, Hodgkin's disease, acute myeloid leukemia, neuroblastoma, germ cell tumors, systemic lupus erythematosus (SLE), systemic sclerosis, amyloidosis, acute lymphoblastic leukemia, chronic myeloid leukemia, chronic lymphocytic leukemia, myeloproliferative disorders, myelodysplastic syndromes, pure red cell aplasia, paroxysmal nocturnal hemoglobinuria, Fanconi anemia, Thalassemia major, sickle cell anemia, severe combined immunodeficiency (SCID), Wiskott-Aldrich syndrome, hemophagocytic lymphohistiocytosis (HLH), mucopolysaccharidosis, Gaucher disease, metachromatic leukodystrophy, adrenoleukodystrophy, ischemia, and atherosclerosis. Such methods of treatment comprise administering to the subject a therapeutically effective amount of the isolated hematopoietic stem cells obtained by the methods described herein, or committed or differentiated progeny thereof.

In some aspects, the isolated hematopoietic stem cells are autologous to the subject in need thereof. In additional aspects, the isolated hematopoietic stem cells are heterologous to the subject in need thereof.

The disclosure also includes a method for testing the toxicity of a compound on a population of hematopoietic stem cells, the method comprising administering the compound to the population of isolated hematopoietic stem cells obtained by the methods described herein and comparing the response of isolated hematopoietic stem cells exposed to the compound to isolated hematopoietic stem cells not exposed to the compound.

In some aspects of the disclosure, the differentiated cell that is programmed into a hematopoietic stem cell is selected from the group consisting of a cell that is derived from endoderm, a cell that is derived from mesoderm, and a cell that is derived from ectoderm. In some aspects, the hematopoietic stem cell is multipotent.

In some aspects of the disclosure, efficiency of programming into hematopoietic stem cells by the methods described herein is achieved at about or at least about 3% with the three-factor combination of GATA binding protein 2 (GATA2), growth factor independent 1B (GFI1B), and c-Fos. In additional aspects, efficiency of programming into hematopoietic stem cells by the methods described herein is achieved at about or at least about 6% with the four-factor combination of GATA binding protein 2 (GATA2), growth factor independent 1B (GFI1B), c-Fos, and ETV6.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION

The disclosure provides methods for direct programming of HSCs, cells obtained by the methods, and methods of treating subjects in need of HSC transplantation. More specifically, the present disclosure provides methods for producing a self-renewing, uncommitted, multipotent somatic stem cell from a differentiated adult cell source and methods for using those multipotent stem cells.

Before any embodiments of the subject matter of the disclosure are explained in detail, it is to be understood that the disclosure is not limited in its application to the details of construction and the arrangement of components set forth in the following description, including the examples. Accordingly, the disclosure embraces other embodiments and is practiced or carried out in various ways.

The section headings as used herein are for organizational purposes only and are not to be construed as limiting the subject matter described.

DEFINITIONS

To aid in understanding the detailed description of the compositions and methods according to the disclosure, a few express definitions are provided to facilitate an unambiguous disclosure of the various aspects of the disclosure.

Unless otherwise defined, all technical and scientific terms used herein have the same meaning as commonly understood by one of ordinary skill in the art to which this disclosure belongs.

The following abbreviations are used throughout.
AA Amino acid
ACLDL Acetylated low density lipoprotein
BMI1 B lymphoma Mo-MLV insertion region 1 homolog
BMT Bone marrow transplant
DNA Deoxyribonucleic acid
Dox Doxycycline
ELISA Enzyme-linked immunosorbent assay
ETV6 ETS translocation variant 6
FACS Fluorescence activated cell sorting
FBS Fetal bovine serum
FOS FBJ osteosarcoma oncogene or c-Fos
GATA2 GATA binding protein 2
GFI1B Growth factor independent 1B
GFP Green fluorescent protein
H2B Histone H2B
HLA Human leukocyte antigen
HSC Hematopoietic stem cell
HSCT Hematopoietic stem cell transplantation
iPSC Induced pluripotent stem cell
MEF Mouse embryonic fibroblast
μM Micromolar
M Molar
mL Milliliter
mM Millimolar
NG Nanogram
PG Picogram
RNA Ribonucleic acid
RUNX1 Runt-related transcription factor 1
SCL Stem cell leukemia
TAL1 T-cell acute lymphoblastic leukemia 1

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The term "gene" refers to a DNA sequence that encodes a sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene is expressed. The term "coding sequence" refers to a DNA sequence that encodes a sequence of amino acids, but does not contain introns or regulatory sequences.

"Nucleic acid" or "nucleic acid sequence" or "nucleic acid molecule" refers to deoxyribonucleotides or ribonucleotides and polymers thereof in either single- or double-stranded form. The term nucleic acid is used interchangeably with gene, complementary DNA (cDNA), messenger RNA (mRNA), oligonucleotide, and polynucleotide. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The terms encompass molecules formed from any of the known base analogs of DNA and RNA such as, but not limited to 4-acetylcytosine, 8-hydroxy-N6-methyladenine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions, in some aspects, are achieved by generating sequences in which the third position of one or more selected (or all) codons is substituted with mixed-base and/or deoxyinosine residues (Batzer et al., Nucleic Acid Res. 19: 5081, 1991; Ohtsuka et al., J. Biol. Chem. 260: 2605-8, 1985; Rossolini et al., Mol. Cell. Probes 8: 91-8, 1994). The term nucleic acid is used interchangeably with gene, cDNA, mRNA, oligonucleotide, and polynucleotide.

The terms "protein," "polypeptide," and "peptide" are used interchangeably herein to refer to a polymer of amino acid residues linked via peptide bonds. The term "protein" typically refers to large polypeptides. The term "peptide" typically refers to short polypeptides.

The terms "identical" or percent "identity" as known in the art refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). "Substantial identity" refers to sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity over a specified sequence. In some aspects, the identity exists over a region that is at least about 50-100 amino acids or nucleotides in length. In other aspects, the identity exists over a region that is at least about 100-200 amino acids or nucleotides in length. In other aspects, the identity exists over a region that is at least about 200-500 amino acids or nucleotides in length. In certain aspects, percent sequence identity is determined using a computer program selected from the group consisting of GAP, BLASTP, BLASTN, FASTA, BLASTA, BLASTX, BestFit and the Smith-Waterman algorithm It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range.

The term "similarity" is a related concept but, in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If, in the same example, there are five more positions where there are conservative substitutions, then the percent identity remains 50%, but the percent similarity would be 75% (15/20). Therefore, in cases where there are conservative substitutions, the degree of percent similarity between two polypeptides will be higher than the percent identity between those two polypeptides.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all.

As used herein "selectable marker" refers to a gene encoding an enzyme or other protein that confers upon the cell or organism in which it is expressed an identifiable phenotypic change such as enzymatic activity, fluorescence, or resistance to a drug, antibiotic or other agent. A "heterologous selectable marker" refers to a selectable marker gene that has been inserted into the genome of an animal in which it would not normally be found. In some aspects, a selectable marker is GFP or mCherry. The worker of ordinary skill in the art will understand which selectable marker known in the art is useful in the methods described herein.

The term "vector" is used to refer to any molecule (e.g., nucleic acid, plasmid or virus) used to transfer coding information to a host cell. A "cloning vector" is a small piece of DNA into which a foreign DNA fragment can be inserted. The insertion of the fragment into the cloning vector is carried out by treating the vehicle and the foreign DNA with the same restriction enzyme, then ligating the fragments together. There are many types of cloning vectors and all types of cloning vectors are included for use in the disclosure. An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. In certain aspects, the expression vector includes a nucleic acid to be transcribed operably linked to a promoter.

The term "coding sequence" is defined herein as a nucleic acid sequence that is transcribed into mRNA, which is translated into a polypeptide when placed under the control of the appropriate control sequences. The boundaries of the coding sequence are generally determined by the ATG start codon, which is normally the start of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences. In one aspect, a promoter DNA sequence is defined by being the DNA sequence located upstream of a coding sequence associated thereto and by being capable of controlling the expression of this coding sequence.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "transduction" as used herein refers to the acquisition and transfer of eukaryotic cellular sequences by retroviruses or lentiviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., Virology, 52:456 (1973); Sambrook et al., Molecular Cloning, a Laboratory Manual, Cold Spring Harbor Laboratories, New York, (1989); Davis et al., Basic Methods in Molecular Biology, Elsevier, (1986); and Chu et al., Gene, 13:197 (1981). Such techniques can be used to introduce one or more exogenous DNA moieties into suitable host cells.

The term "introducing" as used herein refers to the transduction or transfection of exogenous DNA into the cell for subsequent expression of the encoded polypeptide in the cell. In some aspects, the methods of the disclosure include introducing a combination of transcription factors into a differentiated cell.

The term "transformation" as used herein refers to a change in a cell's genetic characteristics, and a cell has been transformed when it has been modified to contain new DNA. For example, a cell is transformed where it is genetically modified from its native state. Following transfection or transduction, the transforming DNA may recombine with that of the cell by physically integrating into a chromosome of the cell. In some instances, the DNA is maintained transiently as an episomal element without being replicated, or it replicates independently as a plasmid. A cell is considered to have been stably transformed or transduced when the DNA is replicated with the division of the cell.

As used herein, the term "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, muscle cell, or endothelial cell). Differentiation occurs in stages, whereby cells gradually become more specified until they reach full maturity, which is also referred to as "terminal differentiation." A "differentiated cell," as used herein, is a cell that has matured so that it has become specialized, i.e., lost its capacity to develop into any specialized cell type found in the body.

As used herein, a "stem cell" is a multipotent, pluripotent, or totipotent cell that is capable of self-renewal and can give rise to more than one type of cell through asymmetric cell division. The term "self renewal" as used herein, refers to the process by which a stem cell divides to generate one (asymmetric division) or two (symmetric division) daughter cells having development potential indistinguishable from the mother cell. Self renewal involves both proliferation and the maintenance of an undifferentiated state. Of all stem cell types, autologous harvesting involves the least risk. By definition, autologous cells are obtained from one's own body, just as one may bank his or her own blood for elective surgical procedures. Heterologous cells, therefore, are cells obtained from another source, not from one's own body.

"Totipotent (i.e., omnipotent) stem cells" can differentiate into embryonic and extra-embryonic cell types. Such cells can construct a complete, viable organism. These cells are produced from the fusion of an egg and sperm cell. Cells produced by the first few divisions of the fertilized egg are also totipotent. "Pluripotent stem cells" are the descendants of totipotent cells and can differentiate into nearly all cells, i.e., cells derived from any of the three germ layers. "Multipotent stem cells" can differentiate into a number of cells, but only those of a closely related family of cells. For example, hematopoietic stem cells are an example of mutlipotent stem cells, and they can differentiate into any of the many types of blood cells, but they cannot become muscle or nerve cells. "Oligopotent stem cells" can differentiate into only a few cell types within a tissue. For example, a lymphoid stem cell can become a blood cell found in the lymphatic system, e.g., T cell, B cell, or plasma cell, but cannot become a different kind of blood cell, such as a red blood cell or a platelet; and a neural stem cell can only create a subset of neurons in the brain. "Unipotent stem cells" can produce only one cell type, their own, but have the property of self-renewal, which distinguishes them from non-stem cells, e.g., muscle stem cells.

The term "multipotent," with respect to stem cells of the disclosure, refers to the ability of the stem cells to give rise to cells of multiple lineages. An "HSC" is self-renewing and is a multipotent cell. Thus, HSCs can be transplanted into another individual and then produce new blood cells over a period of time. In some animals, it is also possible to isolate stem cells from a transplanted individual animal, which can themselves be serially transplanted into other individuals, thus demonstrating that the stem cell was able to self-renew.

The phrase "programming a differentiated cell into a multipotent hematopoietic stem cell" refers to a process whereby treatment of a differentiated cell has brought about a process of de-differentiation in the cell so that the cell now exhibits a multipotent phenotype.

As used herein, the term "isolated" refers to a stem cell or population of daughter stem cells in a non-naturally occurring state outside of the body (e.g., isolated from the body or a biological sample from the body). In some aspects, the biological sample includes bone marrow, synovial fluid, blood (e.g., peripheral blood), or tissue.

As used herein, the term "purified" as in a "purified cell" refers to a cell that has been separated from the body of a subject but remains in the presence of other cell types also obtained from the body of the subject. By "substantially purified" is meant that the desired cells are enriched by at least 20%, more preferably by at least 50%, even more preferably by at least 75%, and most preferably by at least 90%, or even 95%.

A "population of cells" is a collection of at least ten cells. In various aspects, the population consists of at least twenty cells. In other aspects, the population consists of at least one hundred cells. In further aspects, the population of cells consists of at least one thousand, or even one million cells or more. Because the stem cells of the present disclosure exhibit a capacity for self-renewal, they could potentially be maintained in cell culture indefinitely.

The term "allogeneic," as used herein, refers to cells of the same species that differ genetically to the cell in comparison.

The term "autologous," as used herein, refers to cells derived from the same subject.

As used herein, the term "subject" refers to a vertebrate, and in some exemplary aspects, a mammal. Such mammals include, but are not limited to, mammals of the order Rodentia, such as mice and rats, and mammals of the order Logomorpha, such as rabbits, mammals from the order Carnivora, including felines (cats) and canines (dogs), mammals from the order Artiodactyla, including bovines (cows) and swines (pigs) or of the order Perssodactyla, including equines (horses), mammals from the order Primates, Ceboids, or Simoids (monkeys) and of the order Anthropoids (humans and apes). In exemplary aspects, the mammal is a mouse. In more exemplary aspects, the mammal is a human.

The terms "effective amount" and "therapeutically effective amount" each refer to the amount or number of HSCs necessary to elicit a positive response in the subject in need of HSCT or HSC therapy. For example, an effective amount, in some aspects of the disclosure, would be the amount necessary to carry out HSCT in a subject with a disease, disorder, or condition which could benefit from receiving HSCT and elicit a positive effect on the health of the subject.

A "control," as used herein, can refer to an active, positive, negative or vehicle control. As will be understood by those of skill in the art, controls are used to establish the relevance of experimental results, and provide a comparison for the condition being tested.

The term "combination" as used herein refers to two or more molecules or factors. In some aspects, combinations of transcription factors, i.e., two or more transcription factors, are described herein. In various aspects, combinations include, but are not limited to, 3, 4, 5, 6, 7, 8, 9, 10, 11, 12, 13, 14, 15, 16, 17, 18, 19, or 20 transcription factors. In specific aspects, combinations include three transcription factors, four transcription factors, five transcription factors, six transcription factors, and seven transcription factors.

In exemplary aspects, the combination of transcription factors includes, but is not limited to, GATA2, GFI1B, and c-Fos. In additional exemplary aspects, the combination of transcription factors includes, but is not limited to, GATA2, GFI1B, c-Fos, and ETV6. In even more exemplary aspects, the combination of transcription factors includes, but is not limited to, GATA2, GFI1B, c-Fos, ETV6, and one or more of SCL/TAL1, RUNX1, and BMI1.

Transcription Factors of the Disclosure

Various transcription factors are used in the methods of the disclosure. The disclosure includes both mouse and human homologs of the transcription factors listed herein. Variants and analogs with significant identity to the transcription factors described herein below are included for use in the methods described herein.

In some aspects, 18 transcription factors, as discussed herein and set out in Table 1 below, were screened for 34/H2BGFP activation in MEFs.

TABLE 1

Transcription factors screened for 34/H2BGFP activation in MEFs.

| Gene name | Gene Bank |
| --- | --- |
| cFos | NM_010234 |
| Erdr1 | NM_133362 |
| PU.1 | NM_011355 |
| Tcf3 | NM_001164147 |
| Etv6 | NM_007961 |
| Hhex | NM_008245 |
| Scl | NM_011527 |
| Gata2 | NM_032638 |
| Bmi1 | NM_007552 |
| Mllt3 | NM_027326 |
| Meis1 | NM_010789 |
| Trib3 | NM_175093 |
| Bex2 | NM_009749 |
| HoxA9 | NM_010456 |
| Runx1 | NM_009821 |
| Etv3 | NM_012051 |
| Gfi1b | NM_008114 |
| Lyl1 | NM_008535 |

In some aspects, "GATA binding protein 2 (GATA2)" or a homolog thereof, is the transcription factor introduced into a differentiated cell in the methods described herein. GATA2 is a member of the GATA family of zinc-finger transcription factors that are named for the consensus nucleotide sequence they bind in the promoter regions of target genes. The encoded protein plays an essential role in regulating transcription of genes involved in the development and proliferation of hematopoietic and endocrine cell lineages. The disclosure includes, but is not limited to, GATA2 provided in GenBank accession numbers NM_008090.5 (mouse) and M68891.1 (human).

In some aspects, "Growth factor independent 1B (GFI1B)," or a homolog thereof, is the transcription factor introduced into a differentiated cell in the methods described herein. GFI1B is a transcriptional repressor and a target of E2A. GFI1B promotes growth arrest and apoptosis in lymphomas. GFI1B expression in primary T-lymphocyte progenitors is dependent on E2A and excess GFI1B prevents the outgrowth of T lymphocyte progenitors in vitro. GFI1B represses expression of Gata3, a transcription factor whose appropriate regulation is required for survival of lymphomas and T-lymphocyte progenitors. The disclosure includes, but is not limited to, GFI1B provided in GenBank accession numbers AF017275.1 (mouse) and NM_004188.4 (human).

In some aspects, the "FBJ osteosarcoma oncogene or Fos or c-Fos" is the transcription factor introduced into a differentiated cell in the methods described herein. c-Fos is a protein encoded by the FOS gene. Fos is a cellular proto-oncogene belonging to the immediate early gene family of transcription factors. c-Fos has a leucine-zipper DNA binding domain, and a transactivation domain at the C-terminus. Transcription of c-Fos is upregulated in response to many extracellular signals, e.g., growth factors. The disclosure includes, but is not limited to, Fos provided in GenBank accession numbers NM_010234.2 (mouse) and NM_005252.3 (human).

In some aspects, "ETS translocation variant 6 (ETV6)" is the transcription factor introduced into a differentiated cell in the methods described herein. ETV6 is an oncogene that encodes an ETS transcription factor. This gene is known to be involved in a large number of chromosomal rearrangements associated with leukemia and congenital fibrosarcoma. The disclosure includes, but is not limited to, ETV6 provided in GenBank accession numbers NM_007961.3 (mouse) and NM_001987.4 (human).

In some aspects, "stem cell leukemia/T-cell acute lymphoblastic leukemia 1 (SCL/TAL1)" is the transcription factor introduced into a differentiated cell in the methods described herein. SCL/TAL1 expression level is involved in regulating human hematopoietic stem cell self-renewal and engraftment. The disclosure includes, but is not limited to, SCL/TAL1 provided in GenBank accession numbers NM_011527.2 (mouse) and NM_003189.2 (human).

In some aspects, "runt-related transcription factor 1 (RUNX1)" is the transcription factor introduced into a differentiated cell in the methods described herein. RUNX1 is a transcription factor which appears to be involved in acute myeloid leukemia, systemic lupus erythematosus, psoriasis, and rheumatoid arthritis. The disclosure includes, but is not limited to, RUNX1 provided in GenBank accession numbers NM_001111021.1 (mouse) and NM_001754.4 (human).

In some aspects, "B lymphoma Mo-MLV insertion region 1 homolog (BMI1)" or "BMI1 polycomb ring finger oncogene," or "polycomb complex protein BMI-1" is the transcription factor introduced into a differentiated cell in the methods described herein. BMI1 is a transcription factor that has been reported as an oncogene by regulating p16 and p19, which are cell cycle inhibitor genes. In some aspects, BMI1 is also known as FLV12/BMI1, MGC12685, PCGF4, and RNF51. The disclosure includes, but is not limited to, BMI1 provided in GenBank accession numbers NM_007552.4 (mouse) and NM_005180.8.

In some aspects, a combination of transcription factors are introduced into a differentiated cell in the methods described herein. In particular aspects, the combination of transcription factors comprises GATA2, GFI1B, and c-Fos. In more particular aspects, the combination of transcription factors comprises GATA2, GFI1B, c-Fos, and ETV6. In additional aspects the combination of transcription factors comprises GATA2, GFI1B, c-Fos, and one or more transcription factors selected from the group consisting of SCL/TAL1, RUNX1, and BMI1. In more particular aspects, the combination of transcription factors comprises GATA2, GFI1B, c-Fos, ETV6 and one or more transcription factors selected from the group consisting of SCL/TAL1, RUNX1, and BMI1. In further aspects the combination of transcription factors comprises GATA2, GFI1B, and c-Fos and further includes a combination of any of ETV6, SCL/TAL1, RUNX1, and BMI1.

Vectors, Transduction, Transformation, and Methods for Introducing the Transcription Factors into Cells Cloning vectors include all those known in the art. See, e.g., Sambrook, Fritsch & Maniatis, Molecular Cloning: A Laboratory Manual, Second Edition. Cold Spring Harbor, N.Y.: Cold Spring Harbor Laboratory Press, 1989. Expression vectors include all those known in the art, including without limitation engineered chromosomes, mini-chromosomes, cosmids, plasmids (e.g., naked or contained in liposomes), phagemids, and viruses that incorporate the recombinant polynucleotide. The expression vector is inserted or introduced (e.g., via transformation or transduction) into an appropriate host cell for expression of the polynucleotide and polypeptide via transformation or transfection using techniques known in the art. See, e.g., Sambrook, Fritsch & Maniatis, Molecular Cloning: A Laboratory Manual, Second Edition. Cold Spring Harbor, N.Y.: Cold Spring Harbor Laboratory Press, 1989. In one aspect, a retroviral or lentiviral vector is used as the expression vector for insertion of the various transcription factors (TFs) described herein.

After the vector has been constructed and a nucleic acid molecule encoding a TF polypeptide has been inserted into the proper site of the vector, the completed vector is inserted into a suitable host cell for amplification and/or polypeptide expression. The transformation of an expression vector for a TF polypeptide into a selected host cell is, in various aspects, accomplished by well-known methods such as transfection, transduction, infection, calcium chloride-mediated transformation, electroporation, microinjection, lipofection or the DEAE-dextran method or other known techniques. The method selected will in part be a function of the type of host cell to be used. These methods and other suitable methods are well known to the skilled artisan and are set forth, for example, in Sambrook et al., supra.

Host cells, in some aspects, are differentiated cells. In some aspects the differentiated cells are mouse embryonic fibroblasts (MEFs). In further aspects, the differentiated cells include, but are not limited to, mouse tail tip fibroblasts (TTFs), differentiated hematopoietic cells, such as B and T lymphocytes, macrophages, and hematopoietic progenitor cells, human dermal fibroblasts, epithelial cells, and peripheral blood mononuclear cells (PBMCs). In additional aspects, mouse and human ESCs are transduced with a combination of TF genes to improve differentiation toward HSCs.

The host cell, when cultured under appropriate conditions, synthesizes the TF polypeptide(s) which program the cell to undergo dedifferentiation into a multipotent hematopoietic stem cell state. Such host cells include, but are not limited to, host cells of fungal, invertebrate, and vertebrate, e.g., mammalian, sources. For examples of such host cells, see Maniatis et al., Molecular Cloning: A Laboratory Manual, Cold Spring Harbor Laboratory, Cold Spring Harbor, N.Y. (1989). In additional aspects, host cells used in the art since the publication of the Maniatis (supra) manual are also used in the methods disclosed herein.

Mice, Mouse Embryonic Fibroblast (MEF) Isolation and Culture

In some aspects, mice were used and MEFs were isolated and cultured. In one aspect, individual transgenic CD34-tTA (Radomska et al., Blood 100: 4410-19, 2002) and TetO-H2BGFP (Tumbar et al., Science 303: 359-63, 2004) mouse lines were established in the C57BL/6 (CD45.2) background. Double transgenic (designated 34/H2BGFP) MEFs were derived from crosses of the two transgenic mice. Cells from each E14.5 embryo were plated in MEF media, grown for 4-7 days until confluent, and then split once. To identify double transgenic embryos the head, fetal liver and all internal organs were removed and used for genotyping with the following primers: GFP 5'-AGCTGACCCTGAAGT-TCATCTG (SEQ ID NO: 1), GFP 3'-GTCGGCCATGA-TATAGACGTTG (SEQ ID NO: 2) and hCD34 5'-AGAAGAGATGAGGTGTGAGGAT (SEQ ID NO: 3), hCD34 3'-GGATCCACAAGAATGAGCATGTA (SEQ ID NO: 4). The remaining tissue was manually dissociated and incubated in TrypLE Express (Invitrogen) for 15 min to create a single cell suspension. Cells were plated in a 10-cm tissue culture dish in MEF media (Dulbecco's Modified Eagle Medium; Invitrogen) containing 10% FBS (Benchmark), 1 mM L-Glutamine and penicillin/streptomycin (10 µgml-1; Invitrogen). The AFT024 cell line was cultured in MEF media at 32° C. and mitotically inactivated by irradiation as previously described (Moore et al., Blood 89: 4337-47, 1997). MEFs were sorted to remove residual CD45+ and GFP+ cells that could represent cells with hematopoietic potential and cultured for two additional passages before plating for retroviral transduction.

Molecular Cloning and Retrovirus Production

In some aspects, molecular cloning and retrovirus production is carried out. In one aspect, coding regions of each candidate TF were individually cloned into a pMXs vector (Takahashi et al., Cell 126: 663-76, 2006). Virus was generated by calcium phosphate transfection into the Phoenix-ECO packaging cell line (Kinoshita et al., 95: 595-604, 1998). Viral supernatants were harvested after 36, 48 and 72 hours, passed through a 0.45 µm filter and concentrated 40-fold with Amicon ultra centrifugal filters (Millipore).

Retroviral Transduction and Cell Culture

In some aspects, retroviral transduction and cell culture is carried out. In one aspect, 34/H2BGFP MEFs were seeded at a density of 25,000 cells per well on 0.1% gelatin coated 6-well plates and incubated overnight with pools of TF pMXs retroviruses in media supplemented with 8 µg/ml polybrene. Transductions with mCherry in pMXs resulted in >95% efficiency. After 16-20 hours, media was replaced with fresh MEF media. At day 4, post-transduction cells were dissociated with TrypLE Express and 10,000 cells per well were plated on 0.1% gelatin-coated 6-well plates containing mitotically inactivated AFT024 stroma. All cultures were maintained in Myelocult Media (M5300; Stem Cell Technologies) supplemented with hydrocortisone ($10^{-6}$ M; Stem Cell Technologies), with or without 100 ng/ml SCF, 100 ng/ml Flt3L, 20 ng/ml IL-3, and 20 ng/ml IL-6 (R&D), with the exception of methylcellulose cultures where cytokine complete Methocult media (M3434; Stem Cell Technologies) was used. Media was changed every 6 days for the duration of the cultures. In some aspects, emerging GFP+ colonies were counted 21-25 days post-transduction.

Genomic PCR

In some aspects, genomic PCR is carried out. In one aspect, DNA was isolated using phenol-chloroform extraction (Sigma). Presence of integrated retroviral sequences was checked by PCR using Phusion Flash (Thermo Scientific) high-fidelity PCR Master Mix (30 cycles of 98° C. for 1 sec; 60° C. for 5 sec and 72° C. for 15 sec) with primers found in Table 2.

TABLE 2

Primers used to confirm integration of retroviruses by PCR.

| Retrovirus | Forward | Reverse |
|---|---|---|
| PMX-Gfi1b | GACGGCATCGCA GCTTGGATACAC (SEQ ID NO: 5) | GCTCTGGTTC AGCAACATCT (SEQ ID NO: 6) |

TABLE 2-continued

Primers used to confirm integration of retroviruses by PCR.

| Retrovirus | Forward | Reverse |
|---|---|---|
| PMX-HoxA9 | GACGGCATCGCA GCTTGGATACAC (SEQ ID NO: 7) | CTGGCCGAGA GCGGTTCAGG (SEQ ID NO: 8) |
| PMX-Etv3 | GACGGCATCGCA GCTTGGATACAC (SEQ ID NO: 9) | GCGAGCCACT TCATCTGGAT (SEQ ID NO: 10) |
| PMX-Mllt3 | GACGGCATCGCA GCTTGGATACAC (SEQ ID NO: 11) | CAGCAACTTT CTTCTAAAGT (SEQ ID NO: 12) |
| PMX-Meis1 | GACGGCATCGCA GCTTGGATACAC (SEQ ID NO: 13) | CTCTTTAAAG CGTCATTGAC (SEQ ID NO: 14) |
| PMX-Lyl1 | GACGGCATCGCA GCTTGGATACAC (SEQ ID NO: 15) | CAAGTCCAGC TCACTATGGC (SEQ ID NO: 16) |
| PMX-Scl | GACGGCATCGCA GCTTGGATACAC (SEQ ID NO: 17) | CGGCCCTTTA AGTCCCTCGC (SEQ ID NO: 18) |
| PMX-Gata2 | GACGGCATCGCA GCTTGGATACAC (SEQ ID NO: 19) | GTGGTGCTAG GGTCAGGAGA (SEQ ID NO: 20) |
| PMX-Runx1 | GACGGCATCGCA GCTTGGATACAC (SEQ ID NO: 21) | GCTGTCGGTG CGCACTAGC (SEQ ID NO: 22) |
| PMX-Fos | GACGGCATCGCA GCTTGGATACAC (SEQ ID NO: 23) | GATGGGGCCA CGGAGGAGAC (SEQ ID NO: 24) |
| PMX-Etv6 | GACGGCATCGCA GCTTGGATACAC (SEQ ID NO: 25) | CAGGAGGGCC TTGCCATTCA (SEQ ID NO: 26) |

Immunofluorescence

In some aspects, immunofluorescence was used. In one aspect, 34/H2BGFP-derived nuclear GFP detection and colony counting for estimation of efficiency was done directly on 6-well plates under an inverted microscope. For live staining, phycoerythrin (PE)-conjugated sterile rat monoclonal antibodies against Tie2 (Tek4; eBiosciences), CD31 (390; eBiosciences), CD45 (30-F11; BD Biosciences), and Sca1 (D7; eBiosciences), were used at a 1:100 dilution. Emergent colonies were washed once with PBS 5% FBS and incubated with conjugated antibodies for 30 min at room temperature. Biotin-conjugated anti-VE-cadherin (11 D4.1; BD Pharmingen) was used at a 1:100 dilution followed by two washes and incubation with PE-conjugated Streptavidin (eBiosciences) at a 1:200 dilution. Cultures were then washed twice with PBS 5% FBS to remove unbound antibody. Cells were visualized on a Leica DMI4000 microscope and processed with Leica software and Adobe Photoshop. For time-lapse microscopy phase contrast and fluorescent pictures were acquired every 20 min for 96 hours using a ×20 objective and a Leica DMI6000 B microscope using a Leica DFC340 FX camera. Movies were analyzed with Leica and QuickTime softwares.

Hematopoietic Stem Cell isolation, FACS Sorting and Analysis

In some aspects, HSCs are isolated, sorted and analyzed. In one aspect, total bone marrow (BM) cells were harvested from long bones (tibias and femurs) by crushing with pestle and mortar in PBS supplemented with 5% NBCS (New Born Calf Serum, Gibco). Bone debris was filtered away with 70 µm cell strainers (BD). Red blood cells were lysed with ammonium chloride Red Cell Lysis Buffer for 5 min on ice and further filtered through 45 µm cell strainers to obtain a single-cell suspension. Lineage negative, CD48– cells were enriched by immunolabeling BM cells with lineage cocktail antibodies (against CD2, CD3, CD5, CD8, B220, Mac-1, GR-1, Ter 119) and CD48 (OX-78, Pierce) followed by magnetic bead depletion with Goat anti-Rat IgG conjugated Dynabeads (Dynal, Invitrogen). Dead cells were excluded by staining with propidium iodide. To isolate LSK CD48– HSCs, the Lin-CD48– enriched BM cells were stained with goat anti rat Cy5-R-PE (Invitrogen) for the remaining CD48 and lineage markers, and subsequently with Pacific Blue-conjugated Sca1 (D7; Biolegend), allophycocyanin (APC) conjugated cKit (2B8; Biolegend) followed by FACS sorting on an InFlux cell sorter (BD Biosciences). For isolating LSK CD48– Flk2+HSCs, LSK CD48– Flk2– CD34+HSCs, LSK CD48– Flk2-CD34– HSCs, or LSK CD48– Flk2– CD34–CD150+HSCs, Lin– CD48– enriched BM cells were additionally stained with PE-conjugated Flk2 (A2F10.1; eBioscience), Alexa Fluor 700-conjugated CD34 (RAM34; eBioscience), PE-Cy7-conjugated CD150 (TC15-12F12.2; Biolegend). For isolating 34/H2BGFP+Sca1+Prom1+(Day 20), 34/H2BGFP+CD45+cKit+(Day 35) and 34/H2BGFP+CD45+cKit– (Day 35) cell populations, cultures were dissociated with TrypLE Express after transduction and stained with PE-Sca1 and APC-conjugated anti-Prominin1 (13A4, eBioscience) or PE-CD45 and APC-cKit, respectively. Cell populations were isolated on an InFlux cell sorter (BD Biosciences) and immediately lysed in Trizol (Ambion) for RNA extraction or cultured on 0.1% gelatin coated 6-well plates in Myelocult media. Flow cytometric analysis was performed on a 5-laser LSRII with DiVa software (BD Biosciences) and analyzed using FlowJo software. 4,6-diamidino-2-phenylindole (1 µg/mL, Sigma) was added before analysis to exclude dead cells.

Quantitative RT-PCR Analysis

In certain aspects, quantitative RT-PCR is carried out. In one aspect, 100 cells from the indicated samples were sorted directly into a mixture of VILO 5× Reaction Mix (SuperScript VILO cDNA Synthesis Kit, Invitrogen; PN 11754-250), SUPERase-In (Ambion), and NP-40 (Fisher). RNA was denatured at 60° C. for 90 sec and 5 min on ice and reverse transcribed in the presence of 10× Superscript Enzyme Mix (SuperScript VILO cDNA Synthesis Kit) and T4 Gene 32 protein (New England Biolabs) as follows: 5 min at 25° C., 30 min at 50° C., 25 min at 55° C., 5 min at 60° C. and 10 min at 70° C. Specific target pre-amplification was performed with TaqMan PreAmp Master Mix (Invitrogen; PN 4391128) and 500 nM of pooled primer mix by heating at 95° C. for 10 min followed by then 20 cycles of 96° C. for 10 sec and 60° C. for 10 min. Pre-amplified cDNA was exonuclease treated (37° C. for 30 min, New England Biolabs), diluted 5× with DNA suspension buffer (Teknova) and used for the real-time PCR. Gene expression was analyzed using a BioMark 96-96 Dynamic Array (Fluidigm) using 5 µM of gene-specific primers (Table 3) and SsoFast EvaGreen Supermix with Low ROX (Bio-Rad Laboratories, PN 172-5211). The PCR profile was 95° C. for 1 min followed by 30 cycles of 96° C. for 5 sec and 60° C. for 20 sec. Data were analyzed using BioMark Real-Time PCR Analysis Software, Version 3.1 (Fluidigm), Cluster 3.0 and displayed by Java Treeview. Data were normalized according to Hprt expression. The relative abundance of sequences was calculated using the ΔC(T) method.

TABLE 3

Primers used for qRT-PCR amplification using the BioMark 96-96 Dynamic Array.

| Gene | Forward | Reverse |
| --- | --- | --- |
| Acta2 | GAGGCACCACTGAAC CCTAA (SEQ ID NO: 27) | TACATGGCGGGGACA TTGAA (SEQ ID NO: 28) |
| Actb | CCCTAAGGCCAACCG TGAAA (SEQ ID NO: 29) | CAGCCTGGATGGCTA CGTAC (SEQ ID NO: 30) |
| Bex2 | GACTACGCCGCAAGG GATA (SEQ ID NO: 31) | GCATCCTGTGGCTTT TCTTCC (SEQ ID NO: 32) |
| Bmi1 | CCTGTGTGGAGGGTA CTTCA (SEQ ID NO: 33) | TGCTGGTCTCCAAGT AACGTA (SEQ ID NO: 34) |
| Bmp4 | GAACCGGGCTTGAGT ACCC (SEQ ID NO: 35) | GGTCCCTGGGATGTT CTCC (SEQ ID NO: 36) |
| Cd14 | TCTTTCACTGGGCTG AAGCA (SEQ ID NO: 37) | GGTTCCTATCCAGCC TGTTGTA (SEQ ID NO: 38) |
| Cd34 | CCGAGCCATATGCTT ACACA (SEQ ID NO: 39) | ACCTCACTTCTCGGA TTCCA (SEQ ID NO: 40) |
| Cd93 | ACAGCTATTCCTGGG TTCCA (SEQ ID NO: 41) | AGCTGTCTCTAAGGC CACATA (SEQ ID NO: 42) |
| Chd5 | AACGAGGACAGCAAC TTCAC (SEQ ID NO: 43) | TGGCATGCTCCCGAT TAAAC (SEQ ID NO: 44) |
| Cdkn1a | GAACATCTCAGGGCC GAAAAC (SEQ ID NO: 45) | TCTGCGCTTGGAGTG ATAGAA (SEQ ID NO: 46) |
| Cdkn1b | CAGTGTCCAGGGATG AGGAA (SEQ ID NO: 47) | TTCGGGGAACCGTCT GAAA (SEQ ID NO: 48) |
| Cdkn2a | CTTTGTGTACCGCTG GGAAC (SEQ ID NO: 49) | TGGCCGCGAAGTTCC A (SEQ ID NO: 50) |
| Cdkn2d | CTGAACCGCTTTGGC AAGAC (SEQ ID NO: 51) | CCTTGCTTCAGGAGC TCCAA (SEQ ID NO: 52) |
| Cebpa | ATGGCAGTGTGCACG TCTA (SEQ ID NO: 53) | TGGCAAGAATCAGAG CAAAACC (SEQ ID NO: 54) |
| Col3a1 | TGCTGGAAAGAATGG GGAGAC (SEQ ID NO: 55) | GGTCCAGAATCTCCC TTGTCAC (SEQ ID NO: 56) |
| Col5a2 | TTCCAGGGTCTGATG GTTTACC (SEQ ID NO: 57) | TCCTTTAGGCCCCGA AGAAC (SEQ ID NO: 58) |
| Csf1r | GACTGGCTAGGGACA TCATGAA (SEQ ID NO: 59) | TCTGGGGCCATCCAC TTTAC (SEQ ID NO: 60) |
| Csf2ra | CGACGTGGTGGCTAC GAA (SEQ ID NO: 61) | GGTGCAGTGGGAAGA GTTACA (SEQ ID NO: 62) |

TABLE 3-continued

Primers used for qRT-PCR amplification using the BioMark 96-96 Dynamic Array.

| Gene | Forward | Reverse |
| --- | --- | --- |
| Csf3r | GCGTCCAACTCCTGG ATCA (SEQ ID NO: 63) | GAGGTGCATGAGGCA GGATA (SEQ ID NO: 64) |
| Dnmt1 | AGCCATTGGCCTGGA GATTA (SEQ ID NO: 65) | GCAGCCTCCTCTTTT GCTTTA (SEQ ID NO: 66) |
| Dnmt3a | CGCCAGAAGTGCAGA AACA (SEQ ID NO: 67) | AATGAAGAGTGGGTG CTCCA (SEQ ID NO: 68) |
| Dnmt3b | GACGTCCGGAAAATC ACCAA (SEQ ID NO: 69) | GATCATTGCATGGGC TTCCA (SEQ ID NO: 70) |
| Eed | TGGAAGGGCACAGAG ATGAA (SEQ ID NO: 71) | AGAGTGATCCATACC ACAGGAC (SEQ ID NO: 72) |
| Egr1 | ACAACCCTATGAGCA CCTGAC (SEQ ID NO: 73) | GGCTGGGATAACTCG TCTCC (SEQ ID NO: 74) |
| Emcn | TTGCAACCACTCCAT CAACC (SEQ ID NO: 75) | TAACAACCAGCGCGA TAACC (SEQ ID NO: 76) |
| Erdr1 | TCACCCACGAAAGCA CACA (SEQ ID NO: 77) | CTGTGGGGATGGCAG AGAC (SEQ ID NO: 78) |
| Erg | ACGGTTAATGCATGC CAGAA (SEQ ID NO: 79) | TTTGCGTAGCTTCGG GATATAC (SEQ ID NO: 80) |
| Etv2 | CCCTCCAAATCGAAC AAGCA (SEQ ID NO: 81) | GAGGAATTGCCACAG CTGAA (SEQ ID NO: 82) |
| Etv3 | AGGCTGTAGCATCGT GGAAA (SEQ ID NO: 83) | TTGTAGGCCCAATCC GGAAA (SEQ ID NO: 84) |
| Etv6 | GCCATGCCCATTGGG AGAATA (SEQ ID NO: 85) | AAGTTTTCGTACCGG CTGTCA (SEQ ID NO: 86) |
| Ezh2 | TGATGGAAAAGTGCA TGGTGAC (SEQ ID NO: 87) | GACCAAGAGCATTTA CCAACTCC (SEQ ID NO: 88) |
| Fbn2 | TGAGACATGCCCTCC TGTAA (SEQ ID NO: 89) | TGTGATGGGGTTGGG TCTAA (SEQ ID NO: 90) |
| Fli1 | TCTCCTTGGAGGATC ACAGAC (SEQ ID NO: 91) | TTGGCCCCAGGATCT GATAA (SEQ ID NO: 92) |
| Flt3 | CCTTCCCCAACCTGA CTTCA (SEQ ID NO: 93) | GTTGCCACCCATGTT CTGATAC (SEQ ID NO: 94) |
| Flt3l | GTCCCATCTCCTCCA ACTTCAA (SEQ ID NO: 95) | GGCCACAGTGACTGG GTAA (SEQ ID NO: 96) |
| Fn1 | CGTCATTGCCCTGAA GAACA (SEQ ID NO: 97) | AAGGGTAACCAGTTG GGGAA (SEQ ID NO: 98) |

TABLE 3-continued

Primers used for qRT-PCR amplification using the BioMark 96-96 Dynamic Array.

| Gene | Forward | Reverse |
|---|---|---|
| Fos | ATGGGCTCTCCTGTCAACAC (SEQ ID NO: 99) | GCTGTCACCGTGGGGATAA (SEQ ID NO: 100) |
| Fstl1 | GTTCCTCAAGTGCCTCAACC (SEQ ID NO: 101) | TGCATAGGTTTCGTCCTCCA (SEQ ID NO: 102) |
| Gata2 | CACCCCTAAGCAGAGAAGCAA (SEQ ID NO: 103) | TGTGGCACCACAGTTGACA (SEQ ID NO: 104) |
| Gata3 | CCTACCGGGTTCGGATGTAA (SEQ ID NO: 105) | CCGCAGTTCACACACTCC (SEQ ID NO: 106) |
| Gfi1 | TGAGCCTGGAGCAACACA (SEQ ID NO: 107) | AGCGTGGATGACCTCTTGAA (SEQ ID NO: 108) |
| Gfi1b | CCAGGCATGGACACTTACCA (SEQ ID NO: 109) | CGGCGGACATGCACTTCTA (SEQ ID NO: 110) |
| H2afy | GCGGCAAGGAGTTTGTAGAA (SEQ ID NO: 111) | GCCATGGCCTGCACTAATA (SEQ ID NO: 112) |
| Hhex | CTCTCCCCACCCGAGAGAAA (SEQ ID NO: 113) | TAGCTCGGCGATTCTGAAACC (SEQ ID NO: 114) |
| Hlf | TGAAGCCACAGCCCATGATTA (SEQ ID NO: 115) | CCTCGCCCAGTACTTGTCA (SEQ ID NO: 116) |
| Hoxa3 | AGTCAAGGCAGAACACTAAGCA (SEQ ID NO: 117) | CAGGCGGGCTCTTGTCA (SEQ ID NO: 118) |
| Hoxa9 | CTCCGAAAACAATGCCGAGAA (SEQ ID NO: 119) | CGAGTGGAGCGAGCATGTA (SEQ ID NO: 120) |
| Hoxb4 | CCTGGATGCGCAAAGTTCA (SEQ ID NO: 121) | GACCTGCTGGCGAGTGTA (SEQ ID NO: 122) |
| Hprt | CAGTACAGCCCCAAAATGGTTA (SEQ ID NO: 123) | AGTCTGGCCTGTATCCAACA (SEQ ID NO: 124) |
| Id1 | ACCCTGAACGGCGAGATCA (SEQ ID NO: 125) | GATCGTCGGCTGGAACACA (SEQ ID NO: 126) |
| Il11 | GCGGACAGGGAAGGGTTAAA (SEQ ID NO: 127) | CCAGGACCAGGCGACAAA (SEQ ID NO: 128) |
| Il3ra | CTGTGCCCACCCATTCCA (SEQ ID NO: 129) | AGTCTTCAAGAGCTGGTTCCC (SEQ ID NO: 130) |
| Il6ra | GCAGGAATCCTCTGGAACC (SEQ ID NO: 131) | GGACACTCGTTGCTTCTGTA (SEQ ID NO: 132) |
| Itga2b | TGGCAGTCACTGACGTCAAC (SEQ ID NO: 133) | TCTGCCCTGCTCTCCATATACAA (SEQ ID NO: 134) |
| Itgam | AAGCAGCTGAATGGAGGAC (SEQ ID NO: 135) | GCCCCATTGGTTTTGTGAAACA (SEQ ID NO: 136) |
| Jun | GGAAACGACCTTCTACGACGA (SEQ ID NO: 137) | TGGGTTACTGTAGCCGTAGGC (SEQ ID NO: 138) |
| Kdr | ATTTCACCTGGCACTCTCCA (SEQ ID NO: 139) | TCCCAGGAAAGGGTTTCACA (SEQ ID NO: 140) |
| Kit | GTGCCAACCAAGACAGACAA (SEQ ID NO: 141) | TTCCATGATGGCAGGAGTCA (SEQ ID NO: 142) |
| Kitt | GCGGGAATCCTGTGACTGATA (SEQ ID NO: 143) | CGGCGACATAGTTGAGGGTTA (SEQ ID NO: 144) |
| Lmo2 | CTACTACAAGCTGGGACGGAAA (SEQ ID NO: 145) | TCACAGGATGCACAGAGACC (SEQ ID NO: 146) |
| Ly6a | ACCCTGATGGAGTCTGTGTTAC (SEQ ID NO: 147) | AGGGCAGATGGGTAAGCAAA (SEQ ID NO: 148) |
| Lyl1 | AAGCGCAGACCAAGCCATA (SEQ ID NO: 149) | TCACGGCTGTTGGTGAACA (SEQ ID NO: 150) |
| Mbtd1 | CAGGACGGACATTTCGATACAC (SEQ ID NO: 151) | ACCATTCTCCACTCTGGTCTAC (SEQ ID NO: 152) |
| Meis1 | AGTTGGCACAAGATACAGGAC (SEQ ID NO: 153) | GGGCTGCACTATTCTTCTCC (SEQ ID NO: 154) |
| Mll1 | AACAGACTGACCAGCCCAAA (SEQ ID NO: 155) | TTTAATCCGGGGTCCTCGAAC (SEQ ID NO: 156) |
| Mllt3 | TGACTCGGAGATGGAAAGACC (SEQ ID NO: 157) | TGTCACTGCCGTCACTCAA (SEQ ID NO: 158) |
| Mpl | AGCTCAAGAGACCTGCTACC (SEQ ID NO: 159) | CACCGAGAGATGGCTCCA (SEQ ID NO: 160) |
| Myb | TCCTCCGTCAACAGCGAATA (SEQ ID NO: 161) | CAATGCGACAGGATAGGGAAC (SEQ ID NO: 162) |
| Myc | AGTGCTGCATGAGGAGACA (SEQ ID NO: 163) | TCTCCACAGACACCACATCAA (SEQ ID NO: 164) |
| Nfe2 | CCTCCTCAGCAGAACAGGAA (SEQ ID NO: 165) | TGAGGCTCAAAAGATGTCTCAC (SEQ ID NO: 166) |
| Nos3 | GGGATTCTGGCAAGACAGACTA (SEQ ID NO: 167) | GCAGCCAAACACCAAAGTCA (SEQ ID NO: 168) |
| Pecam1 | GCACAGTGATGCTGAACAAC (SEQ ID NO: 169) | GTCACCTTGGGCTTGGATAC (SEQ ID NO: 170) |

TABLE 3-continued

Primers used for qRT-PCR amplification using the BioMark 96-96 Dynamic Array.

| Gene | Forward | Reverse |
|------|---------|---------|
| Pou5f1 | TCCCTACAGCAGATCACTCAC (SEQ ID NO: 171) | CGCCGGTTACAGAACCATAC (SEQ ID NO: 172) |
| Prdm16 | TCCGAAACTTCATCGCCAAC (SEQ ID NO: 173) | CTGTCCAGGTCTTGGATCTCA (SEQ ID NO: 174) |
| Prom1 | GCGATGGACTCTGCTGTTAA (SEQ ID NO: 175) | CCTATGCCGAACCAGAACAA (SEQ ID NO: 176) |
| Pten | GAGACATTATGACACCGCCAAA (SEQ ID NO: 177) | AAGTTCTAGCTGTGGTGGGTTA (SEQ ID NO: 178) |
| Ptprc | TGATGAGGGCAGACTGTTCC (SEQ ID NO: 179) | TCGGGCATCTTTGATGGGAA (SEQ ID NO: 180) |
| Runx1 | AGAACCAGGTAGCGAGATTCA (SEQ ID NO: 181) | ACGGTGATGGTCAGAGTGAA (SEQ ID NO: 182) |
| Sfpi1 | AACAGATGCACGTCCTCGATA (SEQ ID NO: 183) | CATCCGGGGCATGTAGGAA (SEQ ID NO: 184) |
| Sox17 | CAGAACCCAGATCTGCACAAC (SEQ ID NO: 185) | GCTTCTCTGCCAAGGTCAAC (SEQ ID NO: 186) |
| Sox4 | CATGTCCCTGGGCAGTTTCA (SEQ ID NO: 187) | CTGAGCCGGGTTCGAAGTTAA (SEQ ID NO: 188) |
| Spn | TGACCAAGCCTCAGGAAGAA (SEQ ID NO: 189) | GCCCCAAAGAGGAGGAGAA (SEQ ID NO: 190) |
| Suz12 | CCACAGCAGGTTCATCTTCAA (SEQ ID NO: 191) | TTCCTGCATAGGAGCCATCA (SEQ ID NO: 192) |
| Tal1 | AGCCGCTCGCCTCACTA (SEQ ID NO: 193) | ACCCGGTTGTTGTTGGTGAA (SEQ ID NO: 194) |
| Tcf3 | GGCAGCAGTGACCAGAAC (SEQ ID NO: 195) | TGCTGTGGGAGTCACTGAA (SEQ ID NO: 196) |
| Tek | GTTGGATGGCAATCGAATCAC (SEQ ID NO: 197) | CCAGAGCAATACACCATAGGAC (SEQ ID NO: 198) |
| Tert | ACTGAGGAACTCCGTTGTCA (SEQ ID NO: 199) | AGGAAGTGCAGGAAGAAGTCA (SEQ ID NO: 200) |
| Tgfb1 | GCTGCGCTTGCAGAGATTAA (SEQ ID NO: 201) | GTAACGCCAGGAATTGTTGCTA (SEQ ID NO: 202) |
| Thy1 | GCGAATCCCATGAGCTCCAATA (SEQ ID NO: 203) | CTTATGCCGCCACACTTGAC (SEQ ID NO: 204) |
| Trib3 | CGTCGCTTTGTCTTCAGCAA (SEQ ID NO: 205) | ATCACGCAGGCATCTTCCA (SEQ ID NO: 206) |
| Trp53 | CACAGCGTGGTGGTACCTTA (SEQ ID NO: 207) | CCCATGCAGGAGCTATTACACA (SEQ ID NO: 208) |
| Vcam1 | CCCAAACAGAGGCAGAGTGTA (SEQ ID NO: 209) | TGACCCAGATGGTGGTTTCC (SEQ ID NO: 210) |
| Vegfa | CCAGCACATAGGAGAGATGAG (SEQ ID NO: 211) | CTGGCTTTGTTCTGTCTTTCTT (SEQ ID NO: 212) |
| Vim | GATTTCTCTGCCTCTGCCAAC (SEQ ID NO: 213) | CAACCAGAGGAAGTGACTCCA (SEQ ID NO: 214) |
| Vwf | AGTTTGGTGGACCTCATGCA (SEQ ID NO: 215) | GTTACATAGCGCACGGCAAA (SEQ ID NO: 216) |
| Wnt5a | TCCTTCGCCCAGGTTGTTATA (SEQ ID NO: 217) | CAGAGAGGCTGTGCACCTA (SEQ ID NO: 218) |

RNA-Seq Library Preparation, Sequencing and Analysis

In some aspects, FACS-isolated cells were lysed in Trizol (Ambion). RNA integrity was evaluated using a Eukaryotic RNA 6000 Nano chip on an Agilent 2100 Bioanalyzer (Agilent Technologies). Up to 1 µg of total RNA from each sample was used for library preparation with the TruSeq RNA Sample Preparation Kit (Illumina). A common adapter was used for all samples and barcode sequences present in the reverse primer were introduced by 12-16 cycles of amplification (Table 4). In some aspects, each library was assessed for quality and size distribution using an Agilent High Sensitivity Assay bioanalyzer chip and quantified by PCR. Equimolar amounts of each barcoded library were mixed and single-end sequenced on an Illumina HiSeq Sequencing System. For each sample, 14-21.7 M 50-nt reads were obtained, pre-processed with the FASTX-toolkit suite (hannonlab.cshl.edu/fastx_toolkit/) and aligned to the mouse genome (*Mus musculus* mm9 assembly) using TopHat mapper.

TABLE 4

Oligonucleotide Sequences used for mRNA-seq Library Preparation.

| | |
|---|---|
| DNA adapters | 5' GATCGGAAGAGCACACGTCT 3' (SEQ ID NO: 219) |
| | 5' ACACTCTTTCCCTACACGACGCTCTTCCGATC*T 3' (SEQ ID NO: 220) |
| Multiplexing forward primer | 5' AATGATACGGCGACCACCGAGATCTACACTCTTTCCCTACACGACGCTCTTCCGATCT 3' (SEQ ID NO: 221) |
| Reverse primer BC_01 | 5' CAAGCAGAAGACGGCATACGAGAT[CGTGAT]GTGACTGGAGTTCAGACGTGTGCTCTTCCGATCT 3' (SEQ ID NO: 222) |
| Reverse primer BC_02 | 5' CAAGCAGAAGACGGCATACGAGAT[ACATCG]GTGACTGGAGTTCAGACGTGTGCTCTTCCGATCT 3' (SEQ ID NO: 223) |

TABLE 4-continued

Oligonucleotide Sequences used
for mRNA-seq Library Preparation.

| Reverse primer BC_03 | 5' CAAGCAGAAGACGGCATACGAGAT[GCCTAA]GTGACTGGAGTTCAGACGTGTGCTCTTCCGATCT 3' (SEQ ID NO: 224) |
|---|---|
| Reverse primer BC_04 | 5' CAAGCAGAAGACGGCATACGAGAT[TGGTCA]GTGACTGGAGTTCAGACGTGTGCTCTTCCGATCT 3' (SEQ ID NO: 225) |
| Reverse primer BC_05 | 5' CAAGCAGAAGACGGCATACGAGAT[CACTGT]GTGACTGGAGTTCAGACGTGTGCTCTTCCGATCT 3' (SEQ ID NO: 226) |
| Reverse primer BC_06 | 5' CAAGCAGAAGACGGCATACGAGAT[ATTGGC]GTGACTGGAGTTCAGACGTGTGCTCTTCCGATCT 3' (SEQ ID NO: 227) |
| Reverse primer BC_07 | 5' CAAGCAGAAGACGGCATACGAGAT[GATCTG]GTGACTGGAGTTCAGACGTGTGCTCTTCCGATCT 3' (SEQ ID NO: 228) |
| Reverse primer BC_08 | 5' CAAGCAGAAGACGGCATACGAGAT[TCAAGT]GTGACTGGAGTTCAGACGTGTGCTCTTCCGATCT 3' (SEQ ID NO: 229) |

*phosphorothioate
[ ]barcode sequences in brackets mRNA-seq Analysis

In some aspects, mRNA sequence analysis was carried out. In one aspect, post alignment with TopHat release 1.4.1 (Langmead et al., Genome Biol. 10, R25, 2009; Trapnell et al., Bioinformatics: 25, 1105-11, 2009; Trapnell et al., Nat. Biotechnol. 28: 511-5, 2010) against the *Mus musculus* mm9 assembly using the known transcripts option, unmapped reads were matched to the pMXs sequence assembly using Bowtie aligner release 0.12.7 (Trapnell et al., 2009, supra) to determine exogenous gene expression. All resultant .bam files were processed using Samtools version 0.2.5 (Li et al., Bioinformatics 25: 2078-9, 2009) and Bedtools version 2.16.2 (Quinlan et al., Bioinformatics 26: 841-2, 2010) and visualized on the Integrated Genome Browser version 2.1 (Robinson et al., Nat. Biotechnol. 29: 24-6, 2011) or the UCSC Genome Browser (Kent et al., Genome Res. 12, 996-1006, 2002). Transcript assembly and expression estimation was conducted with Cufflinks release 1.3.0 (Trapnell et al., 2010, supra; Roberts et al., Genome Biol. 12: R22, 2011; Trapnell et al., Nat. Protoc. 7: 562-78, 2012) using a *Mus musculus* mm9 reference annotation and upper quartile normalization. Cufflinks assemblies were merged and processed through Cuffdiff for gene FPKM reporting and differential expression analysis. Each library was treated as a separate non-replicate sample. Gene transcript count data from the mRNA-seq analysis was obtained by reprocessing the data through TopHat release 2.0.0 and Cufflinks and Cuffdiff release 2.0.0. Gene set enrichment analysis (GSEA) (Subramanian et al., Proc. Natl. Acad. Sci. USA 102: 15545-50, 2005) between day 20 and CD45+cKit+ or CD45+cKit+ and CD45+cKit– was performed using the FPKM values from output from Cufflinks (Trapnell et al., 2010, supra; Roberts et al., 2011, supra) release 1.3.0 run against the Molecular Signatures Database version 2.0 (Subramanian et al., 2005, supra) curated gene sets (Gene set sizes 0-5000) ranked by Ratio_of_Classes. Non-negative Matrix Factorization (NMF) (Brunet et al., Proc. Natl. Acad. Sci. USA 101: 4164-9, 2004) of the FPKM values obtained from RNA sequencing was performed on the GenePattern Platform (Reich et al., Nat. Genet. 38: 500-1, 2006) using the NMF consensus analysis module at k. initial=2 and k. final=5, and for k=4.

Visualization of FPKM expression density and inter-sample FPKM correlation was conducted in R version 2.15.0 with the CummeRbund package (Trapnell et al., 2012, supra). For the PCA plots (Clark et al., Introduction to statistical methods to analyze large data sets: principal components analysis. Sci Signal. 2011 Sep. 6; 4(190):tr3.) and grid enrichment analysis for the microRNAs and MGI-Mouse Phenotypes, gene counts were extracted with HTSeq, and differentially expressed genes were detected based on a statistical analysis of these counts. The mean-variance relationship was determined by fitting a second order polynomial to the pooled distribution over all gene counts. This allowed for an improved estimate of the variance of each expression value. Individual gene expressions were modeled with a negative binomial distribution and the p-value for the observed pairs of counts (one for each class) was estimated based on these distributions. The p-values were corrected for multiple hypotheses testing by the Benjamini Hochberg method, resulting in sets of differentially expressed genes with a fixed false discovery rate.

Cells and Cell Markers

In some embodiments, methods are provided for programming HSCs from differentiated cells, i.e. de-differentiating cells from a committed or differentiated cell type into a multipotent cell type, i.e., HSC.

The methods of the disclosure include the use of any type of differentiated cell. As described herein, a "differentiated cell" is a cell that has matured so that it has become specialized, i.e., lost its capacity to develop into any specialized cell type found in the body. The disclosure includes all types of differentiated cells for transduction and reprogramming toward HSCs. Such cells include, but are not limited to, various distinct cell types in the body.

Cells that are derived primarily from endoderm include, but are not limited to, gland cells, exocrine secretory epithelial cells, hormone secreting cells, epithelial cells lining internal body cavities, and ciliated cells. Examples of such cells include, but are not limited to, salivary gland mucous cells, salivary gland serous cells, Von Ebner's gland cells, mammary gland cells, lacrimal gland cells, ceruminous gland cells, eccrine sweat gland dark cells, eccrine sweat gland clear cells, apocrine sweat gland cells, gland of Moll cell, sebaceous gland cells, Bowman's gland cells, Brunner's gland cells, seminal vesicle cells, prostate gland cells, bulbourethral gland cells, Bartholin's gland cells, gland of Littre cells, endometrium cells, goblet cells, mucous cells, zymogenic cells, oxyntic cells, acinar cells, Paneth cells, Type II pneumocytes, Clara cells, pituitary cells (e.g., somatotropes, lactotropes, thyrotropes, gonadotropes, and corticotropes), magnocellular neurosecretory cells, intestinal cells, respiratory tract cells, thyroid gland cells, thyroid epithelial cells, parafollicular cells, parathyroid gland cells, chief cells, oxyphil cells, adrenal gland cells, chromafin cells, Leydig cells, theca cells, granulosa cells, corpus luteum cells, juxtaglomerular cells, macular cells, macula densa cells, peripolar cells, mesangial cells, endothelial fenestrated cells, endothelial continuous cells, endothelial splenic cells, synovial cells, serosal cells, squamous cells, columnar cells, dark cells, vestibular membrane cells, basal cells, marginal cells, cells of Claudius, cells of Boettcher, choroid plexus cells, ciliary epithelial cells, corneal endothelial cells, Peg cells, respiratory tract ciliated cells, oviduct ciliated cells, uterine endometrial ciliated cells, rete testis ciliated cells, ductulus deferens ciliated cells, and ciliated ependymal cells.

Cells that are derived primarily from ectoderm include, but are not limited to, keratinizing epithelial cells, wet stratified barrier epithelial cells, sensory transducer cells of the nervous system, autonomic neurons, sense organ and peripheral neuron supporting cells, central nervous system neurons and glial cells, and lens cells. Such cells include, but are not limited to, epidermal keratinocytes, epidermal basal cells, keratinocytes, nail bed basal cells, hair shaft cells, hair root sheath cells, hair matrix cells, surface epithelial cells of stratified squamous epithelium, basal epithelial cells, urinary epithelial cells, auditory inner and outer hair cells of organ of Corti, basal cells of olfactory epithelium, cold-sensitive primary sensory neurons, heat-sensitive primary sensory neurons, Merkel cells, olfactory receptor neurons, pain-sensitive primary sensory neurons, photoreceptor cells of the retina (e.g., rod cells, blue-sensitive cone cells, green-sensitive cone cells, and red-sensitive cone cells), proprioceptive primary sensory neurons, touch-sensitive primary sensory neurons, type I carotid body cells, type II carotid body cells, type I and type II hair cells of vestibular apparatus of ear, type I taste bud cells, cholinergic neurons, adrenergic neurons, peptidergic neurons, inner and outer pillar cells of organ of Corti, inner and outer phalangeal cells of organ of Corti, border cells of organ of Corti, Hense cells of organ of Corti, vestibular apparatus supporting cells, taste bud supporting cells, olfactory epithelium supporting cells, Schwann cells, satellite cells, enteric glial cells, astrocytes, neurons, oligodendrocytes, Spindle neurons, anterior lens epithelial cells, and crystallin-containing lens fiber cells.

Cells that are derived primarily from mesoderm include, but are not limited to, metabolism and storage cells, barrier function cells, kidney cells, extracellular matrix cells, contractile cells, blood and immune system cells, pigment cells, germ cells, nurse cells, and interstitial cells. Such cells include, but are not limited to, hepatocytes, adipocytes (e.g., white fat cells and brown fat cells), liver lipocytes, glomerulus parietal cells, glomerulus podocytes, proximal tubule brush border cells, Loop of Henle thin segment cells, distal tubule cells, collecting duct cells, type 1pneumocytes, centroacinar cells, nonstriated duct cells (e.g., principal cells and intercalated cells), duct cells, intestinal brush border cells, exocrine gland striated duct cells, gall bladder epithelial cells, ductus deferens nonciliated cells, epididymal prinicipal and basal cells, ameloblast epithelial cells, planum semilunatum epithelial cells, Organ of Corti interdental epithelial cells, loose connective tissue fibroblasts, corneal fibroblasts, tendon fibroblasts, bone marrow reticular tissue fibroblasts, nonepithelial fibroblasts, pericytes, nucleus pulposus cells, cementoblasts, cementocytes, odontoblasts odontocytes, hyaline cartilage chondrocytes, fibrocartilage chondrocytes, elastic cartilage chondrocytes, osteoblasts, osteocytes, osteoprogenitor cells, hyalocytes, stellate cells (i.e., of the ear, liver, and pancreas), skeletal muscle cells (e.g., red skeletal muscle cells (slow), white skeletal muscle cells (fast), intermediate skeletal muscle cell, nuclear bag cells of muscle spindle, and nuclear chain cell of muscle spindle), satellite cells, heart muscle cells (e.g., ordinary heart muscle cells, nodal heart muscle cells, and Purkinje fiber cells), smooth muscle cell, myoepithelial cells, erythrocytes, megakaryocytes, monocytes, connective tissue macrophages, epidermal Langerhans cells, osteoclasts, dendritic cells, microglial cells, neutrophil granulocytes, eosinophil granulocytes, basophil granulocytes, mast cells, helper T cells, suppressor T cells, cytotoxic T cells, natural killer T cells, B cells, natural killer cells, reticulocytes, stem cells and committed progenitors of the blood and immune system, melanocytes, retinal pigmented epithelial cells, oogonium, oocytes, spermatids, spermatocytes, spermatogonium cell, spermatozoan, ovarian follicle cells, Sertoli cells, thymus epithelial cells, and interstitial kidney cells.

In some aspects, differentiated cells are fibroblasts. In more particular aspects, the fibroblasts are MEFs. In more particular aspects, the MEFs are double-transgenic 34/H2BGFP MEFs derived from huCD34tTA/TetO-H2BGFP (34/H2BGFP) mouse embryos and used as a reporter cell line. In this model, the GFP reporter is turned on only when the cells have an undifferentiated hematopoietic or endothelial phenotype.

In further aspects, however, methods of the disclosure include the use of all types of differentiated cells. Thus, examples of such differentiated cells include, but are not limited to, the cells identified hereinabove.

HSCs are stem cells that form blood and immune cells. HSCs are ultimately responsible for the constant renewal of blood and produce up to billions of new blood cells each day. HSCs are multipotent stem cells that give rise to all the blood cell types from the myeloid (including, but not limited to, monocytes and macrophages, neutrophils, basophils, eosinophils, erythrocytes, megakaryocytes/platelets, and dendritic cells), and lymphoid lineages (including, but not limited to, T-cells, B-cells, and NK-cells).

An exemplary method for proving that a cell is indeed an HSC is based on the proof described in mice many years ago. Cells are injected into a mouse that has received a dose of irradiation sufficient to kill its own blood-producing cells. If the mouse recovers and all types of blood cells reappear (bearing a genetic marker from the donor animal), the transplanted cells are deemed to have included stem cells.

In another aspect, HSCs are identified by their small size, large nuclear to cytoplasmic ratio, and other properties. In some aspects, precursor HSCs are identified by screening the cell for expression of a hemogenic endothelial cell marker or a multipotent HSC marker, or by uptake of acetylated low density lipoprotein (acLDL).

In a further aspect, an exemplary method for identifying an HSC is performed by labeling the cell with a marker that appears on the surface of the cell. Cell surface markers are widely used according to methods known in the art to identify cells and HSCs express a wide variety and combination of markers. Such cell markers, in some aspects, are tagged with monoclonal antibodies bearing a fluorescent label and analyzed or isolated with fluorescence-activated cell sorting (FACS). In some aspects, markers for human HSCs include, but are not limited to, CD31, CD34, $CD38^{lo/-}$, CD41, CD43, CD45, CD49f, Thy1/CD90, CD105, CD117/c-kit, CD133, CD150, Sca-1, Tie2, VE-Cadherin, KDR/FLK1, Flk-2/Flt3, CXCR4. In particular aspects, acLDL and lectin are coupled to fluorescent markers and bind on the cell surface.

HSCs are negative for the markers that are used for detection of lineage commitment, and are, thus, called Lin⁻. Thus, in some aspects, the methods of the disclosure include screening a cell for a lack of expression of a differentiated hematopoietic lineage (lin) marker, i.e., screening for a Lin⁻ cell. In some aspects, therefore, a lin⁻ marker includes, but is not limited to, CD4, CD5, CD8, CD45RA/B220, Gr-1/Ly-6G/C, and Ter119.

Not all stem cells, however, are covered by the above-recited combinations. The worker of ordinary skill in the art will understand which marker(s) is/are useful in the methods described herein.

Most, if not all, of these markers are available commercially. Such markers include, for example, CD133-APC, SCA-1-PE, Tie2-PE, CD11b-APC, CD31-PE, CD41-APC; and VE-cadherin (eBioscience, San Diego, Calif.); CD45-PE, Flk1-PE, and CD43-APC (BD Biosciences, Sparks, Md.); c-kit-APC (BioLegend®, San Diego, Calif.); and acLDL-DiI (Biomedical Technologies, Inc., Stoughton, Mass.). Marker expression profiles on the GFP+ cells are analyzed by analytical flow cytometry and FACS.

After screening multipotent HSCs for the expression of appropriate hematopoietic markers, HSCs are isolated. Cells are isolated by any method known in the art including, but not limited to, FACS. In some aspects, the HSCs are isolated and frozen with a cryoprotectant. Methods of freezing cells are well known in the art, and all such methods of freezing cells are included for use in the disclosure. Isolated HSCs are available for treatment of a subject in need thereof, for freezing, for further experimentation, or for further cell culture. In additional aspects, the isolated HSCs are further co-cultured with other cells including, but not limited to, stromal cells. In some aspects, the isolated HSCs are autologous to the subject in need thereof. In some aspects, the isolated HSCs are heterologous to the subject in need thereof.

Cell Culture

Cells are cultured using standard media well known to the skilled artisan. The media usually contains all nutrients necessary for the growth and survival of the cells. In some aspects, additional nutrients are added as needed. Suitable media for culturing eukaryotic cells include Roswell Park Memorial Institute medium 1640 (RPMI 1640), Minimal Essential Medium (MEM), Dulbecco's Modified Eagle Medium (DMEM), and Myelocult Medium (Stem Cell Technologies, M5300 and H5100), all of which, in some instances, are supplemented with serum and/or growth factors as indicated by the particular cell line or type being cultured.

Typically, an antibiotic or other compound useful for selective growth of transduced or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

In some aspects, the transduced cells are cultured on gelatin or co-cultured on irradiated cells of another cell line with or without a combination of cytokines. In some aspects, the HSCs are cultured in optimized conditions in serum-free culture medium.

Methods of Use

HSCs are produced in order to undergo differentiation into cells of a hematolymphoid phenotype. The production of such HSCs also allows for the study of the cellular and molecular biology of events of human and mouse development, generation of differentiated cells for use in transplantation (e.g., autologous or allogenic transplantation), treating diseases (e.g., any described herein), in vitro drug screening or drug discovery, disease modeling, and cryopreservation.

Transplantation and Treatment of Disease

HSCs of the disclosure are used in hematopoietic stem cell transplantation (HSCT). HSCT is a procedure in which multipotent progenitor cells, such as HSCs, blood stem cells, or umbilical cord blood capable of reconstituting normal bone marrow function, are administered to a patient. This procedure is often performed as part of therapy to eliminate a bone marrow infiltrative process, such as leukemia, or to correct congenital immunodeficiency disorders. Recent work in this field has expanded its use to allow patients with cancer to receive higher doses of chemotherapy than the bone marrow can usually tolerate; bone marrow function is then salvaged by replacing the marrow with previously harvested stem cells.

The disclosure includes the treatment of a subject who suffers from a condition or disease which could benefit from HSCT, thus making them a candidate for HSCT. In some aspects, such subjects suffer from multiple myeloma or leukemia and they are undergoing prolonged treatment with, or are already resistant to, chemotherapy. In some aspects, candidates for HSCT include pediatric cases where the patient has an inborn defect such as severe combined immunodeficiency or congenital neutropenia with defective stem cells, and also children or adults with aplastic anemia who have lost their stem cells after birth. Other conditions that benefit from HSCT include, but are not limited to, sickle-cell disease, myelodysplastic syndrome, neuroblastoma, lymphoma, Ewing's Sarcoma, Desmoplastic small round cell tumor, chronic granulomatous disease and Hodgkin's disease. More recently non-myeloablative, or so-called "mini transplant," procedures have been developed that require smaller doses of preparative chemotherapy and radiation. This has allowed HSCT to be conducted in the elderly and other patients who would otherwise be considered too weak to withstand a conventional treatment regimen.

HSCs of the disclosure have the potential to differentiate into a variety of cell types including, but not limited to, all cell types of a hematopoietic lineage. Accordingly, HSCs of the disclosure can be transplanted into a subject to treat a number of conditions or diseases which could benefit from HSCT including, but not limited to, cancer, congenital disorders, or vascular disease. More specific conditions or diseases which could benefit from HSCT include, but are not limited to, multiple myeloma, leukemia, congenital neutropenia with defective stem cells, aplastic anemia, myelodysplastic syndrome, neuroblastoma, lymphoma, Ewing's Sarcoma, Desmoplastic small round cell tumor, chronic granulomatous disease, non-Hodgkin's lymphoma, Hodgkin's disease, acute myeloid leukemia, neuroblastoma, germ cell tumors, systemic lupus erythematosus (SLE), systemic sclerosis, amyloidosis, acute lymphoblastic leukemia, chronic myeloid leukemia, chronic lymphocytic leukemia, myeloproliferative disorders, myelodysplastic syndromes, pure red cell aplasia, paroxysmal nocturnal hemoglobinuria, Fanconi anemia, Thalassemia major, sickle cell anemia, severe combined immunodeficiency (SCID), Wiskott-Aldrich syndrome, hemophagocytic lymphohistiocytosis (HLH), mucopolysaccharidosis, Gaucher disease, metachromatic leukodystrophy, adrenoleukodystrophy, ischemia, and atherosclerosis.

The disclosure therefore provides a new technology so that individuals can bank their own fibroblasts to later make personalized HSCs should a need arise in the future for the individual.

Disease Modeling

HSCs can be generated to model and study hematological diseases in vitro. HSCs of the disclosure, in various aspects, are generated from subjects with conditions or diseases including, but not limited to, multiple myeloma, non-Hodgkin's lymphoma, Hodgkin's disease, acute myeloid leukemia, neuroblastoma, germ cell tumors, systemic lupus erythematosus (SLE), systemic sclerosis, amyloidosis, acute lymphoblastic leukemia, chronic myeloid leukemia, chronic lymphocytic leukemia, myeloproliferative disorders, myelodysplastic syndromes, aplastic anemia, pure red cell aplasia, paroxysmal nocturnal hemoglobinuria, Fanconi anemia, Thalassemia major, sickle cell anemia, severe combined immunodeficiency (SCID), Wiskott-Aldrich syndrome, hemophagocytic lymphohistiocytosis (HLH), inborn errors of metabolism, e.g., mucopolysaccharidosis, Gaucher disease, metachromatic leukodystrophies, adrenoleukodystrophies, and a variety of vascular disorders including, but not limited to, ischemia and atherosclerosis. The disclosure, therefore, provides a new technology so that disease-specific HSCs are generated for disease modeling and research. HSCs can be differentiated to any cell type of hematopoietic lineages to dissect in vitro the molecular mechanisms of hematological malignancies.

Pharmaceutical Compositions

Pharmaceutical compositions are also included in the disclosure. In some aspects, a pharmaceutical composition of the disclosure comprises a population of HSCs and a pharmaceutically acceptable diluent, carrier or medium. The phrase "pharmaceutically acceptable" refers to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like. In all aspects, the carriers of the disclosure have to be appropriate for delivery with live cells.

HSCs are generally administered intravenously by routine clinical practice. Dose is dependent upon source of the stem cells (e.g., bone marrow, mobilized peripheral blood cells, and cord blood) and the donor (e.g., autologous and allogeneic, including HLA-matched/mismatched). A typical dose includes, but is not limited to, a dose in the range of $5\text{-}10^6$ cells/kg.

Toxicology Screening

In various aspects, HSCs of the disclosure are used in toxicity screening. For example, assays are used to test the potential toxicity of compounds on the HSCs or the differentiated progeny thereof. In one example, where the HSCs are differentiated into a hematopoietic lineage, hematopoietic stem cells and progenitor assays can be used to investigate growth and differentiation of cells in response to positive and negative regulators of hematopoiesis. These assays provide the opportunity to assess the potential toxicity of compounds on specific hematopoietic (e.g. myeloid, erythroid) cell populations. For example, some assays to assess toxicity of compounds on hematopoietic cells have been described by Van Den Heuvel et al. (Cell Biol. Toxicol. 17: 107-16, 2001), Kumagai et al. (Leukemia 8:1116-23, 1994), and in U.S. Patent Application Publication Nos. US2004/0029188, US2008/0248503, and US2011/0008823.

Other approaches include, prior to applying the drug, transforming the cells with a promoter activated by metabolic or toxicologic challenge operably linked to a reporter gene. Exemplary promoters include those which respond to apoptosis, respond to DNA damage, respond to hyperplasia, respond to oxidative stress, are upregulated in liver toxicity, are responsive to receptors that act in the nucleus, upregulate hepatocyte enzymes for drug metabolism, are from genes which are deficient in particular disease conditions, and genes which regulate synthesis, release, metabolism, or reuptake of neurotransmitters. See, for example, the methods and exemplary promoters in U.S. Patent Application Publication No. 2006/0292695.

In some aspects, for example, HSC progeny of a selected cell type can be cultured in vitro and used for the screening of potential therapeutic compositions. These compositions can be applied to cells in culture at varying dosages, and the response of the cells monitored for various time periods. Physical characteristics of the cells can be analyzed, for example, by observing cell growth with microscopy. The induction of expression of new or increased levels of proteins such as enzymes, receptors and other cell surface molecules, or other markers of significance (e.g., neurotransmitters, amino acids, neuropeptides and biogenic amines) can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Preservation of Cells

Once isolated and/or purified, it is sometimes desirable to preserve the HSCs of the disclosure. In some aspects, HSCs are preserved by freezing in the presence of a cryoprotectant, i.e., an agent that reduces or prevents damage to cells upon freezing. Cryoprotectants include sugars (e.g., glucose or trehalose), glycols such as glycerol (e.g., 5-20% v/v in culture media), ethylene glycol, and propylene glycol, dextran, and dimethyl sulfoxide (DMSO) (e.g., 5-15% in culture media). Appropriate freezing conditions (e.g., 1-3° C. per minute) and storage conditions (e.g., between −140 and −180° C. or at −196° C., such as in liquid nitrogen) can be determined by one of skill in the art.

Other preservation methods are described in U.S. Pat. Nos. 5,004,681, 5,192,553, 5,656,498, 5,955,257, and 6,461,645. Methods for banking stem cells are described, for example, in U.S. Patent Application Publication No. 2003/0215942.

Each publication, patent application, patent, and other reference cited herein is incorporated by reference in its entirety to the extent that it is not inconsistent with the present disclosure.

Recitation of ranges of values herein are merely intended to serve as a shorthand method for referring individually to each separate value falling within the range and each endpoint, unless otherwise indicated herein, and each separate value and endpoint is incorporated into the specification as if it were individually recited herein.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Additional aspects and details of the disclosure will be apparent from the following examples, which are intended to be illustrative rather than limiting.

Example 1

Transduction of Transcription Factors and Screening for Hematopoietic Cell Phenotype To test the hypothesis that hematopoietic stem cells (HSCs) are controlled by a limited set of key transcription factors (TFs) whose expression can redirect differentiated cells to a self-renewing HSC state with the capacity for multipotent differentiation, a combinatorial and systematic overexpression of selected TFs in somatic cells coupled with fluorescent reporter analysis was carried out.
Identification of Transcription Factor Candidates Important for HSC Programming Two approaches were taken to identify candidate reprogramming transcription factors: 1) genome-wide transcriptional profiling to uncover overrepresented genes in HSC, and 2) data-mining the literature and compiling transcriptional regulators identified in other HSC gene expression and functional studies.
Evaluating Reprogramming Towards HSCs—Cell Fate Through Combinatorial Transcription Factor Overexpression From these approaches, an initial set of 18 candidate TFs were selected and DNA encoding each of these 18 TFs was introduced individually into a retroviral vector previously shown to be effective in reprogramming. Specifically, coding sequences from cDNA were amplified and inserted into a retrovirus-based overexpression cassette (pMX) (Takahashi et al., Cell 126: 663-76, 2006). The transgene is expressed under the Moloney leukemia virus LTR promoter. In a control experiment, more than 98% of mouse and human fibroblasts have shown high expression of a reporter (mCherry) using this cassette.

The 18 TFs were combinatorially expressed in double-transgenic 34/H2BGFP MEFs derived from huCD34tTAx/TetO-H2BGFP (34/H2BGFP) mouse embryos and used as a reporter cell line. In this system, the first transgene contains the human CD34 promoter driving the expression of the tet-transactivator (tTA) which activates the second transgene containing the Tet Response Element (TRE) driving the expression of a Histone 2B GFP (H2BGFP) fusion protein that is incorporated into chromatin (Schaniel et al., Ann. N.Y. Acad. Sci. 1176: 26-35, 2009). In the hematopoietic hierarchy, the huCD34 promoter continually directs expression of H2BGFP, specifically in the primitive stem and progenitor compartments. Because this is a Tet-Off system, administration of doxycycline (Dox) turns off H2BGFP expression. With each cell division, the GFP label is diluted by one half, allowing isolation of HSCs on the basis of their divisional history, with quiescent cells that have not divided retaining the highest levels of GFP label. Label-retaining cells are nearly homogeneous in terms of in vivo hematopoietic reconstituting activity following transplantation. In this cell population, novel transcriptional regulators overrepresented in the GFP-high population of HSCs were identified.

The 34/H2BGFP MEFs were transduced with pools of retroviral vectors containing the 18 candidate TFs. The individual expression vectors were first determined to have the same relative infection efficiency and expression levels of the selected cDNA. Transduction was done with the m-Cherry virus alone or the m-Cherry reporter in combination with all 18 candidate TFs. Viral infections were carried out in 2 ml of DMEM supplemented with 10% fetal calf serum, 2 mM L-glutamine, antibiotics (10 μg/ml penicillin and streptomycin) and 6 μg/ml Polybrene. MEFs were cultured for four days in 3 ml of DMEM supplemented with 10% fetal calf serum, 2 mM L-glutamine, and antibiotics.

Four days after transduction, MEF cells were dissociated with TrypLE Express (Gibco) and replated onto the HSC-supporting stromal cell AFT024 (mitotically inactivated) feeder layers. The cells were co-cultured for 17-19 days in Myelocult Media (Stem Cell Technologies, M5300) supplemented with hydrocortisone or other growth factors and analyzed by immunofluorescence. MEFs transduced with PMX-mCherry or the cocktail of 18 factors plus mCherry were analyzed by immunofluorescence at day 21.

HSCs were maintained in Myelocult Media (Stem Cell Technologies, M5300) supplemented with hydrocortisone or other growth factors. In some aspects, such growth factors included, but were not limited to, 1-50 ng/ml (e.g., about 5-15 ng/ml) platelet-derived growth factor-BB (PDGF-BB), 1-50 ng/ml (e.g., about 5-15 ng/ml) epidermal growth factor (EGF), 1-50 ng/ml (e.g., about 5-15 ng/ml) insulin-like growth factor (IGF), or 100-10,000 IU (e.g., about 1,060) LIF, with $10^{-10}$ to $10^{-8}$ M dexamethasone or other appropriate steroid, 2-10 μg/ml linoleic acid, and 0.05-0.15 μm ascorbic acid.

Co-culture of transduced fibroblasts (i.e., HSCs) was carried out in Myelocult Media (Stem Cell Technologies, M5300) supplemented with hydrocortisone on irradiated layers of the stromal cell line AFT024 (Moore et al., Blood 89: 4337-47, 1997; Nolta et al., Leukemia 16: 352-61, 2002) in 6-well plates or large culture dishes with or without the following combination of cytokines: SCF (100 ng/ml), Flt3L (100 ng/ml), IL-3 (20 ng/ml), and IL-6 (20 ng/ml). In certain aspects, thrombopoietin (Tpo) and/or megakaryocyte growth factor were added to the culture medium. In additional aspects, serum-free medium was used for HSC culture.

The emergence of colonies that were organized into structures was only observed in the 18 factor pool and not in the mCherry vector control. Brightfield (BF) microscopy showed colony morphology and mCherry (red) the MEF-origin of reprogrammed colonies. MEFs transduced with the 18 factors were stained with anti-CD45 antibody at day 21 after transduction. Staining with anti-CD45 antibodies revealed patches of CD45+ cells only in cultures of MEFs transduced with the 18 TFs.

Screening was performed based on the activity of the huCD34/H2BGFP transgene, i.e., by examining GFP expression. This transgene is not expressed in differentiated cells, such as MEFs, but the transgene is expressed in HSCs and endothelial progenitors. The elimination was carried out by individual subtraction of factors from the pool of 18 factors. Viruses were produced to overexpress different combinations of factors and the removal of crucial factors led to absent or reduced huCD34 transgene activation, while the removal of inhibitory factors led to an increase in efficiency. Several rounds of elimination were carried out until reaching a minimal combination of three factors, i.e., GATA2, GFI1B, and c-Fos, and an optimal combination of four factors, i.e., GATA2, GFI1B, c-Fos, and ETV6. The initial pool of 18 factors was reduced to 14, then to seven, and finally to four or to three factors. The removal of factors led to an increase in efficiency and the extent of huCD34 transgene reactivation. When 18 factors were used, transgene activation efficiency was approximately 0.01%. The efficiency of huCD34 transgene activation increased to about 3% for when the core combination of three transcription factors, i.e., Gfi1 b, Gata2 and Fos, was used. That efficiency increased to about 6% when the four-factor combination of Gfi1 b, Etv6, Gata2 and Fos was used.

The minimal combination of three factors, i.e., GATA2, GFI1B, and c-Fos, means that the removal of any one of these factors completely abolishes induction of huCD34 transgene. A more optimal combination of four factors includes the three-factor core combination, i.e., Gfi1 b, Gata2 and Fos, plus ETV6. Such four-factor combination increases efficiency of transactivation, but does not abolish induction. Expression of each of the transgenes was determined by Q-RT-PCR.

34/H2BGFP MEFs transduced with the four factor combination of TFs, i.e., GFI1B, GATA2, Fos, and ETV6, were stained with anti-CD45 antibody and analyzed by FACS at days 25, 35 and 45 after transduction. Staining with anti-CD45 antibodies revealed a population of GFP+CD45+ cells only in cultures of MEFs transduced with the combination of 4 TFs. The population of GFP+CD45+ cells increases from 2.8% (day 25) to 7.1% (day 35), to 19.1% (day 45). CD45+GFP-cells were not detected in the cultures. Putative HSCs, cells double positive for CD34+(GFP) and CD45+, were isolated by FACS. Such cells were then either transplanted or stored for later transplantation.

In some colonies, nuclear GFP labeling/fluorescence reflecting the activation of the 34/H2BGFP transgene, i.e., indicative of HSC status, was observed. In one aspect, the three-factor combination of GFI1B, Fos, and GATA2 provided a number of HSC colonies per 10,000 cells that were positive for GFP fluorescence, indicative of a multipotent stem cell phenotype that is inducing the huCD34 promoter. In exemplary aspects, a four-factor combination of GFI1B, Fos, GATA2 and ETV6 provided an even greater number of HSC colonies per 10,000 cells. Transduction of the four-factor combination led to the appearance of huCD34+ colonies at an efficiency of approximately 6% efficiency, whereas transduction of the three-factor combination led to the appearance of huCD34+ colonies at an approximate efficiency of 3%. This showed that the core combination, e.g. the three-factor combination, can redirect differentiated cells into an HSC state. However, the four-factor combination achieved the same result with greater efficiency.

In additional aspects, the introduction of additional transcription factors, such as, stem cell leukemia (SCL), runt-related transcription factor 1 (RUNX1), and B lymphoma Mo-MLV insertion region 1 homolog (BMI1), are included in a seven-factor combination. However, removal of these factors increases the number and extent of huCD34 transgene activation. The identified transcription factors are evolutionary conserved and allow the application of this technology in the future to humans and the field of regenerative medicine.

Because CEBPα plus PU.1 transductions of fibroblasts have been shown to convert fibroblasts into macrophages (Feng et al., Proc. Natl. Acad. Sci. USA 105:6057-62, 2008), direct transdifferentiation of fibroblasts to macrophages was added as a control experiment for the specificity of the huCD34 transgene. MEFs transduced with CEBPα plus PU.1 acquire the mature macrophage marker Mac1 and the pan-hematopoietic marker CD45 but do not activate the huCD34 transgene. Such experiments were carried out and confirmed the specificity of the four-factor combination (Fos, Gfi1 b, Gata2 and Etv6) for induction of HSCs and activation of huCD34 transgene.

Example 2

Characterization of the GFP+ Cells

In preliminary experiments, the number of GFP+ cells in the transduced cultures was low (approximately 0.01%), making extensive characterization challenging. Rare groups of CD45+ cells in the 18-factor transductions that were not GFP+ were also identified. Without being bound by theory, these CD45+/GFP− cells may be more mature hematopoietic cells that result from transiently expressing GFP+ precursors. In contrast, with the optimal 4-factor reprogramming cocktail, the number of GFP+ cells in transduced cultures is high (about 6%). GFP+ cells and other cells types/structures that appear in these cultures can be further characterized.

Because the human CD34 promoter is also active in endothelial cells, the expression of endothelial markers (e.g., CD31, VE-Cadherin, and Tie2) is examined by immunofluorescence. Should the GFP+ cells that form rounded structures be endothelial precursors, the colonies are further examined to determine if they have a hemogenic endothelium phenotype. In addition to expression of human CD34 reporter, reprogrammed cells expressed the somatic stem cell marker Sca-1 and Prominin1 (CD133) at day 20 after transduction. Later, at day 40, colonies were identified that co-express the huCD34 reporter and the hemogenic endothelium markers, Tie2, CD31, and Ve-Cadherin, and show the ability to uptake acetylated low density lipoprotein (acLDL)-Dil. These markers are common to endothelial and hematopoietic cell lineages, and demonstrate the stepwise induction of stem cell characteristics and hemogenic endothelium in culture. Remarkably, those colonies also start to express the pan-hematopoietic marker CD45 (19% of GFP+ cells at day 45). The hematopoietic nature of the budding cells is examined using markers of the hemogenic endothelium, including, but are not limited to, markers for the emergence of HSCs including, but not limited to, CD11b, CD31, CD34, CD41, CD43, CD45, CD117, CD150, Sca-1, c-Kit, Tie2, VE-Cadherin, KDR/FLK1, Flk-2/Flt3, and acLDL. These markers are available commercially [e.g., CD133-APC, SCA-1-PE, Tie2-PE, CD11b-APC, CD31-PE, CD41-APC; and VE-cadherin (eBioscience, San Diego, Calif.); CD45-PE, Flk1-PE, and CD43-APC (BD Biosciences, Sparks, Md.); c-kit-APC (BioLegend®, San Diego, Calif.); and acLDL-Dil (Biomedical Technologies, Inc., Stoughton, Mass.)]. Marker expression profiles on the GFP+ cells are analyzed by analytical flow cytometry and FACS.

Cells expressing a phenotype for hemogenic endothelium can give rise to HSCs and hematopoietic cells.

Transcriptional Profiling of Programmed Cells

High-throughput microfluidics (FLUIDIGM)-based gene expression profiling was used to follow reprogramming progression to HSC cell fate. To characterize the appearance of HSC and hemogenic endothelium markers in 34/H2BGFP-positive cells were profiled using the FLUIDIGM BioMark System. The BioMark 96.96 Dynamic arrays perform 9,216 Q-RT-PCRs per array, assessing the expression of 96 genes across 96 different samples (Spurgeon et al., PLoS One 3(2): e1662, 2008). 34/H2BGFP MEFs were transduced with pools of seven, five, four, and three factors. After four days, cells were transferred onto AFT024 cells and co-cultured for 20 or 40 days in the presence or absence of cytokines. Non-transduced 34/H2BGFP MEFs were included as controls, as 34/H2BGFP MEFs transduced with mCherry alone. Viable cells from control non-transduced MEFs, and mCherry+ controls were sorted into 96-well trays (100 cells/sample in duplicate or triplicate). Transduced samples were sorted for viable GFP+ cells similarly.

Bona fide bone marrow HSC populations isolated from 34/H2BGFP mice were also profiled. These cells demonstrated the following cell surface phenotypes: LSKCD48-; LSKCD48-Flk2+(Multipotent progenitors (MPP)); LSKCD48-Flk2-CD34+(Short Term-(ST-HSC)); LSKCD48-Flk2-CD34− (Long Term-(LT-HSC)); and LSKCD48-Flk2-CD34-CD150+(LT-HSC). LSKCD48-Flk2-CD34-CD150+(LT-HSC) are highly enriched for robust repopulating ability. Major gene expression changes were observed from starting MEFs to transduced cells (day 20 post-transduction) and more importantly to transduced cells (day 40 post-transduction) directly demonstrating that the transduced MEFs are being transcriptionally reprogrammed and 34/H2BGFP+ cells show transcriptional changes over time in culture.

Clustering analysis placed day 40 34/H2BGFP+ cells closer to bona fide HSC than to the remaining samples. Cells expressing fibroblast-specific genes, such as Vim, Acta2, Fn1 and Fbn2, show a marked reduction from day 0 to day 20 demonstrating that signature fibroblast gene expression was extinguished after transduction with the 4 factor combination. In addition, the expression of Prominin (Prom1) and Ly6a (Sca-1) was detected at high levels at day 20, confirming previous observations that Prom 1 and Sca-1 are co-expressed in 34/H2BGFP+ cells at the protein level.

The levels of marker expression did not seem to change significantly between the sorted populations generated with different pools of factors (as long as the core set of factors, i.e., GATA2, GFI1B, and c-Fos, is present) or with the addition of cytokines. Such results suggest that the different factors have an impact on the efficiencies of 34/H2BGFP+ cell generation, but not on their overall gene expression profiles. Remarkably, the activation of HSCs markers, such as Mpl, Erg and c-kit, were detected in day 40 cultures. Endothelial and endothelial progenitor markers, such as Vwf, Nos3, and Id1 were also detected. Reassuringly, the pan-hematopoietic marker CD45 was also detected by immunofluorescence at day 40, but not at day 20. Gene expression analyses at day 40 demonstrated that both three and four factor combinations and selection based on the activation of the 34/H2BGFP reporter yields cells with activated hemogenic endothelial markers that give rise to potential HSCs.

Example 3

Characterizing the Transgene-Free Programmed Hematopoietic Stem Cells

The objective of this study is to generate transgene-free HSCs. Cells are transduced to express the 4-factor combination of GFI1B, Fos, GATA2 and ETV6 in excisable or inducible (Tet-off) lentiviral vectors, followed by a determination of the capacity of the directly programmed HSCs to develop into fully functional HSCs with the capacity to self-renew and differentiate in vivo into all lineages of the hemato-lymphoid system. Assays are carried out to further characterize the programmed stem and progenitor cells.

Without being bound by theory, it is hypothesized that once HSC fate is specified, continued overexpression of the four-factor combination of GFI1B, Fos, GATA2 and ETV6 is detrimental to their ability to differentiate appropriately. This has been documented in iPS reprogramming to pluripotency. To test the hypothesis, the four-factor TF combination of GFI1B, Fos, GATA2 and ETV6 is expressed in floxed lentiviruses that can be excised with tamoxifen-inducible Cre-recombinase after optimal HSC specification.

A floxed lentivirus was engineered using a pHAGE2-STEMCAA backbone (Sommer et al., Stem Cells 28:64-7, 2009) called pHAGE2-mCherry (pHAGE2-EF1a-MCS-IRES¬ mCherry-W-loxP). The four TFs are expressed using this vector to verify that the same phenotype emerges. The TF transgenes are excised from the GFP+HSC marker+ cells that are also mCherry+. Appropriate excision is monitored by the loss of mCherry+ cells and the continued expression of GFP and HSC markers. Excision is accomplished by lentiviral expression of CreERT2 fusion protein, which allows for the control of CRE recombinase by the addition of tamoxifen. Appropriate expression and loss of TF expression upon excision is confirmed by q-RT-PCR. Lentivirus is prepared for each of the candidate TFs and is quality controlled for proper expression and excision efficacy.

In parallel, programmed HSCs are produced with inducible lentivirus (Tet-off) and with minimal genetic manipulation using modified RNAs as described by Warren et al. (Cell Stem Cell 7(5): 618-30, 2010). Modified RNAs for the four-factor network are produced and delivered daily to MEFs, which allows for the isolation of HSCs with no genetic footprint for therapy.

Transgene-free reprogrammed HSCs are tested in a variety of in vitro hematopoietic progenitor assays. The development of characteristic cobblestone area forming cells (CAFC) is assessed in the co-culture of reprogrammed fibroblasts with AFT024. CAFC are phase-dense clusters of cells that develop underneath the stromal monolayer and, at least under some conditions, appear to originate from the most primitive HSCs. This assay system and other quantitative in vitro clonogenic assays, including colony-forming cells (CFC), long term culture-initiating cells (LTC-IC), and limiting dilution CAFC after LTC (LTC-CAFC) are performed. The AFT024 co-culture system maintains LTC-CAFC and LTC-IC that have a high correlative and predictive frequency for long-term repopulating, self-renewing HSC. The simultaneous expression of GFP and HSC markers is determined before (in m-Cherry$^+$ cells) and after excision (in m-Cherry$^-$ cells). The function of reprogrammed HSC is assessed with or without the constitutive overexpression of the four reprogramming TFs. These cells are sorted by FACS and plated onto AFT024 LTCs for CAFC and LTC-IC and also put into standard CFC assays.

The presence of the 34/H2BGFP transgene in these cells allows for the determination of appropriate GFP expression in the HSC/progenitor hierarchy as well as the establishment of a dormant HSC pool in the bone marrow of engrafted animals. Comparative gene expression analyses are carried out to determine the similarities and differences of the directly programmed HSCs with bona fide adult HSCs.

Example 4

Investigating the Functional Properties of Reprogrammed Hematopoietic Stem Cells While activation of reporter and initiation of a signature transcription program gives good indication of cell fate induction, it remains unclear whether these reprogrammed HSCs are true long-term repopulating HSCs. Thus, functional testing of reprogrammed HSCs using in vitro assays is carried out.

Reprogrammed human and mouse GFP+ cells are FACS-sorted and co-cultured with the supportive stromal cell line AFT024 (Moore et al., Blood 89: 4337-47, 1997; Nolta et al., Leukemia 16: 352-61, 2002) in the presence of the cytokine cocktail (Kit and Flt3 ligand, TPO, IL3 and IL6) to promote self-renewal of HSCs. Assays for colony-forming units in culture (CFU-C), cobblestone area forming cells (CAFC), and long-term culture initiating cells (LTC-IC) are used to assess HSC function.

Cultures of MEFs transduced with the four-TF combination, i.e., GATA2, GFI1B, c-Fos, and ETV6, are monitored for the appearance of CAFC as GFP+ cells develop. GFP+ CD45+ cells are co-cultured with AFT024 that maintains LTC-CAFC and LTC-IC that have a high correlative and predictive frequency for long term in vivo repopulating self-renewing HSC. During our programming experiments induced by the four-TF combination (using excisable lentivirus) the simultaneous expression of GFP and HSC markers are determined before (in m-Cherry$^+$ cells) and after (in m-Cherry$^-$ cells) excision. These cells are sorted by FACS and plated in AFT024 LTCs for CAFC and LTC-IC generation and also put into standard CFC assays to measure more committed progenitor cells. For detection and quantification of more committed progenitors (BFU-E, CFU-GM, CFU-G, CFU-M and CFU-GEMM), cells are plated in methylcellulose-containing media (Stem Cell Technologies, Methocult M3434) enriched with hematopoietic differentiation cytokines, such as, EPO, SCF, IL-6 and IL-3.

Example 5

In Vivo Transplantation of Directly Programmed HSCs

To test the long-term reconstitution capacity of reprogrammed HSCs, in vivo assays, such as limiting dilution transplantation and serial transplantation, are carried out. To determine the ability of isolated HSCs to repopulate lethally irradiated animals, experiments are carried out using the congenic CD45.2/CD45.1 competitive repopulation and radioprotection systems. The 34/H2BGFP mice express the CD45.2 allele and, therefore, so do the programmed HSC described herein in the examples set forth above.

Isolated HSCs are transplanted into congenic SJLCD45.1 mice in both competitive repopulation and radioprotection assays. Competitive repopulation assays do not necessitate that the test (donor) cells will rescue the recipient (host) from lethal irradiation. Lethal irradiation for a C57Bl/6 mouse is 1000 rads. All mice will die within two weeks of irradiation if not rescued by bone marrow (BM) transplantation. A CD45.1 mouse is used as the host strain and donor of the competitor cells. The test population from the transduced 34/H2BGFP MEFs is mixed with 2-4×10$^5$ host whole bone marrow cells. This dosage contains sufficient stem and progenitor cells to allow rescue of all recipients of the test cells. Transplantation is, in various aspects, carried out in limiting-dilution amounts to determine the frequency of HSC in the test cell population according to Poisson Statistics. These amounts can range dramatically from one to thousands of test cells depending on the estimate of stem cell frequency in the population being tested. This assay in limiting dilution will be used when we can determine these estimates from positive in vitro results.

Initial experiments are accomplished with unsorted cell populations or cells that are sorted after transduction for GFP+ and stem cell marker+ antigens in estimated amounts according to the number of appropriate cells obtained from sorting. It is difficult to estimate these amounts a priori. An equivalent dose of cells is used for all test and control conditions, plus the addition of one standard dose of competitor BM. For radioprotection assays no competitor BM is given, and test cells are required to rescue the animal from lethal irradiation. Again it is difficult to estimate a priori the dose, but presumably larger doses are required in the range of about a thousand sorted cells per recipient.

Appropriate differentiation is determined by periodic bleeding of the animals and CD45.2+ lineage contribution. Self-renewal potential of the cells is determined by secondary transplantation assays. The expression of various components of the hematopoietic hierarchy and expression of GFP in the BM of the reconstituted mice is also characterized. To characterize the appropriate expression of GFP in stem/progenitor compartments after reconstitution with CD45.2 cells, BM is removed and analyzed for the expression of appropriate cell surface markers and for GFP level. Long-term (LT), short-term (ST), and multipotent progenitor (MPP) HSC compartments are analyzed. Upon achieving appropriate reactivation of the transgene in the programmed HSC, mice are placed on Doxycycline (Dox)-treated water in order to stop expression of GFP. GFP expression is diluted by one-half with each cell division. Thus, this dilution of GFP expression allows for assessing whether the transplanted reconstituted animals are capable of reestablishing a dormant stem cell population. The mice are maintained on Dox for approximately four months. After that, their BM is analyzed as described previously for cell surface marker expression and GFP expression. The reconstituted animals are also treated with Dox and the animals are examined for the appearance of a dormant label-retaining HSC in an appropriate temporal manner.

Example 6

Directed Differentiation of 34/H2BGFP Induced Pluripotent Stem Cells to Hematopoietic Stem Cells In preliminary experiments, iPSC were generated from 34/H2BGFP MEFs using the Piggyback transposon system (Yusa et al., Nat. Methods 6: 363-9, 2009) that allows the precise transgene excision after reprogramming.

iPSC were made from TetO-H2BGFP single transgenic MEFs in the same manner to serve as controls. Multiple lines were generated and characterized by standard protocols (Ang et al., Cell 145: 183-97, 2011; Carvajal-Vergara et al., Nature 465: 808-12, 2010; and Tsai et al., Stem Cells 29: 964-71, 2011). iPSCs are directed towards hematopoietic differentiation by standard protocols Orion et al., Development 137:2829-39, 2010) adapted by ESC/iPSC shared resource facility. Standard protocols first differentiate ESC/iPSC to embryoid bodies (EBs) for 48 hours and these are then disaggregated and induced to mesoderm with Activin A, BMP4, and VEGF for another 48 hours. All cultures are done in serum-free media (StemPro-34 SFM). At this time, a large proportion of the cultured cells are Flk1+ mesodermal cells. These cells are then assayed for their hematopoietic potential, usually in cytokine enriched suspension cultures. In addition, iPSC are transduced with lentivirus driving the expression of GFI1B, GATA2, FOS and ETV6 to induce differentiation towards HSC cell fate.

This protocol is followed and the temporal activation of the 34/H2BGFP transgene is examined by immunofluorescence. The expression of mouse CD34, its overlapping expression with GFP and endothelial markers (e.g., CD31 and Ve-cadherin), as well as hematopoietic markers, is determined. Standard protocols are followed for hematopoietic induction.

Example 7

Cells with Activated 34/H2BGFP Express Endothelial and Hematopoietic Genes

To further characterize gene expression in GFP+ cells, the Fluidigm BioMark System was used as set out above in Example 2. Reporter MEFs were transduced with pools of 7, 5, 4 or 3 TFs and cultured with AFT024 for 20 and 40 days with and without cytokines. Non-transduced and mCherry transduced MEFs, as well as GFP+ cells from TF-transduced samples, were sorted into 96-well plates (100 cells/sample/well in duplicate or triplicate). Gene expression patterns were compared to BM HSPC populations isolated from 34/H2BGFP mice. Dramatic gene expression changes in transduced cells (relative to MEFs) were observed at days 20 and 40. GFP+ cells show time-dependent transcriptional changes, highlighting the dynamic nature of the induction process. Unsupervised hierarchical clustering placed day 40 GFP+ cells generated without cytokines closest to bona fide HSCs. As set out in Example 2, decreased expression of fibroblast-specific genes, such as Vim, Acta2, Fn1, and Fbn2, was observed between days 0 and 20. At day 20, high levels of Prom1 and Ly6a were detected, as was activation of KitL, Csf1r, CD34, and Il3ra. Expression profiles do not show major differences in GFP+ cells generated with different TF pools, as long as Gata2, Gfi1 b, and cFos were present. Thus, the additional factors affect the efficiency, but not the global reprogramming, of gene expression. At day 40, co-expression of hematopoietic (Csfr, Il3r CD43, cKit, Mpl, CD45, and CD41) and endothelial/endothelial progenitor markers (Vwf, Nos3 and Id1) was detected. At day 40, markers of emergent and fetal HSCs (CD93/AA4.1, CD41 and Sox17) and hemogenic endothelium (Etv2 and Runx1) were detected. Using specific primers, expression of endogenous Gata2 was also demonstrated.

Example 8

Sequential Induction of Precursor and Hemogenic Colonies with GATA2, GFI1B, CFOS AND ETV6

To further characterize emerging cells, the expression of Sca1 and Prom1 were examined. After 22 days, 50-60% of the GFP+ cells are Sca1+ and 36% are Prom1+. Prom1+ cells also express high levels of Sca1 (89%), confirming mRNA analyses carried out in day 20 GFP+ cells. The four TF cocktail (Gata2, Gfi1b, cFos, and Etv6) induced higher percentages of GFP+Prom1+ cells in comparison to combinations of 7 or 5, and other combinations of 4 factors. At 35 days, the emergence of colonies containing clusters of non-adherent GFP+ cells was observed. Clusters that express the endothelial markers Tie2, CD31, VE-Cadherin and the pan-hematopoietic marker CD45 were identified.

Experiments were then carried out to determine optimal conditions for generating hematopoietic cell clusters. With the four TF cocktail (Gata2, Gfi1 b, cFos, and Etv6), AFT024 was no longer necessary to generate day 20 GFP+ or day 35 non-adherent hematopoietic cell clusters. In addition, inclusion of cytokines decreased the numbers of non-adherent cells. Cultures on gelatin, without cytokines, yielded 9% CD45+ cells at day 35. The effects of individual cytokines were tested and found that IL-6 is inhibitory (2% CD45+) while IL-3 has a positive effect (27% CD45+). Without being bound by theory, the positive effect of IL-3 may be due to the expansion of CD45+ cells or maturation from precursor endothelial-like cells, as previously reported in mouse aorta-gonad-mesonephros (AGM). Kinetic analyses of endothelial and hematopoietic markers showed that Tie2 expression is transient, while CD45 expression increases steadily over time. This is consistent with the role of Gfi1b in loss of endothelial identity (Lancrin et al., Blood 120: 314-22, 2012).

Between days 30 and 40, several cellular components in GFP+ cultures associated with emergence of CD45+ cells were identified: small non-adherent or semi-adherent GFP+ CD45+ cells with compact nuclei, large adherent GFP+ CD45-cells often found in the margins of circular structures and very large adherent GFP+CD45– cells that contain one or more nucleus/nuclei. CD45+ cells are often seen in association with GFP+CD45– cells, particularly when semi-adherent. The emergence of CD45+ cells was monitored by time-lapse imaging for morphology, reporter activation and live staining for CD45. Small GFP+CD45– cells were found to be associated with large adherent cells. Acquisition of CD45 was often accompanied by dissociation of non-adherent cells from large cells that then die.

In order to determine if the precursor for the emergent hematopoietic cells could be isolated, the GFP+Sca1+Prom1+ population of cells was isolated and cultured on gelatin. After 6 days, a higher percentage (53%) of CD45+ cells was observed in cultures initiated with the sorted cells compared to cultures initiated with an unsorted population of cells (9%). CD45+GFP+ cells emerged in association with large flat CD45-GFP+ cells that were Mac1-negative. Without being bound by theory, these data suggest that GFP+Sca1+Prom1+ cells are hemogenic precursors.

Example 9

Precursor GFP+ Cells Display an Endothelial-Like Gene Expression Signature

To better define the precursor and emergent hematopoietic cells, mRNA sequencing (mRNA-seq) was carried out on cell populations generated after transduction with Gata2, Gfi1 b, cFos and Etv6. Two biological replicates of non-transduced MEFs, day 20 GFP+Sca1+Prom1+ cells, and cKit+ and cKit– subsets of the day 35 GFP+CD45+ population, were sorted. Replicates correlated with each other, in contrast to comparisons between different samples. Non-negative matrix factorization, coupled with consensus clustering, was used to analyze sample diversity, and showed that MEFs are followed by day 20 cells and day 35 cKit+ and cKit– cells. These findings were consistent with morphological changes and the Fluidigm data (set out above). Metagene analysis showed sets of (1) genes expressed in MEFs and silenced in all other samples, (2) genes expressed transiently at day 20, and (3) genes expressed in CD45+cKit+ cells and silenced or also expressed in CD45+cKit− cells. Metagenes, identified in CD45+cKit+ and CD45+cKit− cells, showed higher overlap than those in MEFs and at day 20. Principal component analysis (PCA) placed MEFs, day 20 and day 35 CD45+ cells very distant from each other, demonstrating the striking phenotypic transition from MEFs to day 20 precursors, and subsequently to CD45+ cells. CD45+cKit+ and CD45+cKit− are closely related but clearly distinguishable by PCA.

Alignment of reads at individual gene loci and quantification by fragments per kilobase of exon per million fragments mapped (FPKM) values confirm silencing of MEF genes, i.e., Acta2, Fbn1, Fbn2, Fn1 and Col5a2. Ly6a was upregulated 6-fold at day 20 while Ly6e was upregulated 2.8-fold in CD45+cKit+ cells. Both Ly6a and Ly6e genes encode the Sca1 antigen. CD45 was only detected in day 35 CD45+ cells. At day 20, proposed markers of AGM HSC precursors, including Podocalaxyn-like protein 1 (Pclp-1), and the angiotensin-converting enzyme (ACE) were detected. Pclp-1, Podxl2 and ACE are upregulated 120-, 5-, and 9-fold, respectively. Pro-angiogenic factors such as Hand2, Kdr, Tgfb2, Itga6, Notch4, KitL and Proliferin 2/3 (Plf-2/3) were also detected at day 20. Indeed, pathway analysis using the Panther classification system showed enrichment of pathways related to endothelial biology. Such analysis gave the following values: angiogenesis (p-value=2.5 E-04), Vegf (p-value=5.0 E-04), Tgfβ (p-value=1.3 E-03), integrin signaling (p-value=1.8 E-04), heterotrimeric G-protein signaling, endothelin signaling, and cytokine-mediated inflammation. Gene ontology (GO) analysis showed that extracellular region/matrix, actin cytoskeleton, and cell junctions were enriched cellular component categories. Top molecular function and biological process GO categories were protein and receptor binding, receptor activity, cell communication and signal transduction. Together, these analyses demonstrate that in GFP+Sca1+Prom1+ precursors, an endothelial-like gene expression program precedes the activation of a hematopoietic program in emerging CD45+ cells.

Example 10

Emergent Hematopoietic Cells Express Markers of Definitive Hematopoiesis

Analysis of genes upregulated in day 35 CD45+cKit+ cells, using the mouse genome informatics (MGI) mouse mutant phenotype database, showed that genetic perturbations cause largely hematopoietic phenotypes. In contrast, genes upregulated at day 20 impact blood vessel and embryo development, as well as other processes. Gene set enrichment analysis (GSEA) was used to compare the transition of day 20 precursors to day 35 CD45+cKit+ cells with published gene sets. Significant enrichment of GSEA database HSC gene sets in the CD45+cKit+ samples (24 out of 35 HSC gene sets; Fisher's exact test, p-value=6.6 E-04; FDR<0.25) was found. Indeed, the most enriched gene set among the 1888 in the database was an HSC set. MicroRNA (mir) target prediction focused on genes activated from day 20 to day 35 CD45+cKit+ cells showed highest enrichment of mir-125 targets (p-value=8.48 E-04). Mir-125 is highly expressed in HSCs and has been shown in the art to expand HSC numbers in vivo. Targets of several other mirs implicated in HSPCs (mir-29, mir-142, mir-19, mir-130, and mir-520) were also identified. In contrast, at day 20, a different set of mir targets was identified, including those for vascular endothelium-specific mir-15 (p-value=8.56 E-03) and others (mir-99, mir-200, mir-519, and mir-135) related to endothelial cell biology.

Global analysis also revealed activation of HSC transcriptional regulators, including Scl, Fli1, Hhex, Smad6, Lyl1, Lmo2, Runx1, Sox17, Msi2 and Gfi1. Master regulators of the lymphoid (Ikzf1), myeloid (PU.1) and erythroid lineages (Eto2 and Fog1) were also expressed in CD45+cKit+ and CD45+cKit− cells. Genes were then analyzed in the Notch signaling pathway because of its role in the onset of definitive, but not primitive, hematopoiesis. Notch1 and Notch2 were both upregulated in CD45+ cells, with Notch 1 being more highly expressed in CD45+cKit+ cells and Notch 2 more highly expressed in CD45+cKit− cells. Cxcr4, another marker of definitive hematopoiesis in the Cxcr4 pathway, was expressed in CD45+ cells along with downstream genes. Collectively, these results highlight the definitive hematopoietic nature of cells programmed by the 4 TFs.

Example 11

Specified CD45+Ckit+Cells Silence Retroviral Vectors and Contain a Subpopulation with an HSC Gene Expression and Cell Surface Phenotypes HSCs and primitive progenitors have been shown to silence Moloney-based retrovirus. Moloney virus-based retrovirus (pMXs) proviral expression was analyzed by aligning mRNA-seq reads against the pMXs sequence. Retroviral sequences were detected at day 20, consistent with transgene expression. In CD45+ cells, pMXs sequences were detected in the CD45+cKit− compartment with a 10-fold reduction in CD45+cKit+ cells, which was consistent with silencing in more primitive cells. GSEA was used to compare CD45+cKit+ to CD45+cKit− cells. Consistent with PCA, fewer gene sets were enriched in the CD45+cKit+ to CD45+cKit− comparison than in comparisons to day 20 cells. Four HSC gene sets were enriched, including three from long term (LT)-HSCs. More significant enrichment of LT-HSC gene sets was found in the CD45+cKit+ sample (3 out of 3 LT-HSCs gene sets; Fisher's exact test p-value=5.1 E-05, FDR<0.35).

To determine if this shift in global gene expression was reflected in an LT-HSC cell surface phenotype, additional observations were made. Among Sca1+ cells, 17% were also CD45+ and GFP+. This compartment contained cells with a CD48-CD150+cKit+HSC phenotype, whereas the CD45− compartment did not. These data provide further support that the four transcription factors: GATA2, GFI1B, c-Fos, and ETV6 can program a cell into a multipotent HSC.

Example 12

GATA2, GFI1B and CFOS Induce Colonies that Contain Cells with Human HSC-Like Surface Phenotypes To determine whether human HSC are controlled by a limited set of key TFs similar to those in the mouse, key combinations of transcription factors, e.g., Gata2/Gfi1b/cFos/Etv6 (i4TFs) or Gata2/Gfi1b/cFos (i3TFs), were overexpressed in human dermal fibroblasts (HDFs).

HDFs were infected with pFUW-mOrange+pFUW-M2rtTA (>95% transduction efficiency) or pFUW-Gata2/Gfi1b/cFos/Etv6+pFUW-M2rtTA (i4TFs) and cultured for 20 or 30 days in gelatin-coated dishes with human Myelocult media (H5100, Stem Cell Technologies).

The emergence of colonies with human HSC-like surface phenotypes was observed when HDFs were transduced with such TF combinations, but not with the control mOrange transduction. Colonies were assayed for CD34 expression 30 days after i4TF transduction. HDFs were transduced with i4TF, i3TF (pFUW-Gata2/Gfi1 b/cFos) or control (M2rtTA-only), stained, and CD34+ and CD34− colonies were counted by immunofluoresence at day 30. Data showed that 8.4% of these colonies contained CD34+ cells. In human cells, the combination of 3 transcriptions factors (i.e., i3TFs) yielded more CD34− (191±18, 1.90% efficiency) and CD34+(16±1.7, 0.16% efficiency) colonies than in mouse cells. Colony numbers were per 10,000 infected HDFs (mean±SEM). The decreased efficiency compared to the mouse was expected, because human cells have been reported to be more resistant to reprogramming (Vierbuchen et al., Nat. Biotechnol. 29:892-907, 2011). Colonies were assayed by immunofluorescence for CD34 or CD49f expression 30 days after i3TF transduction. CD34+ or CD49f+ cell morphology was examined.

Results were confirmed by flow cytometry and transducing human foreskin fibroblasts (BJs). Flow cytometry analysis of CD34 and CD49f expression in HDFs and BJs 26 days after transduction with i3TFs was carried out. Transductions with M2rtTA alone were used as a control. A large population of cells expressed CD49f+(26-34%), whereas CD34 expression was more restricted (0.8-1.3%) in transduced HDFs or BJs. CD38 expression was not detected at any time-point. Expression of CD90 and CD49f in gated CD34+ or CD34− cells in transduced HDF or BJ was observed. CD34+ cells expressed CD90 and 59-61% expressed CD49f. Expression of CD45 and Prom1 in gated CD34+ CD49f+ cells in transduced HDF or BJ was also observed. Percentages of Prom1+CD45+, Prom1+CD45− and Prom1-CD45− cells were measured. Among CD34+CD49f+ cells, 9-14% expressed Prom1 and low levels of CD45. These results demonstrate that Gata2, Gfi1 b and cFos impose human HSC-like phenotypes in fibroblasts, as it has been reported by Notta et al. (Science 333:218-221, 2011) that the phenotype of human HSCs has been identified as CD34+ CD38-CD49f+CD90+.

The disclosure has been described in terms of particular embodiments found or proposed to comprise specific modes for the practice of the disclosure. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for programming a differentiated cell into a hematopoietic stem cell, the method comprising introducing a combination of transcription factors in the differentiated cell, wherein the combination comprises GATA binding protein 2 (GATA2), growth factor independent 1B (GFI1B), and c-Fos.

2. The method of claim 1, wherein the combination of transcription factors further comprises ETS translocation variant 6 (ETV6).

3. The method of claim 1, wherein the combination of transcription factors further comprises a transcription factor selected from the group consisting of stem cell leukemia (SCL/TAL1), runt-related transcription factor 1 (RUNX1), and B lymphoma Mo-MLV insertion region 1 homolog (BMI1).

4. The method of claim 1 further comprising the step of screening the hematopoietic stem cell for:
(a) expression of a hemogenic endothelial cell marker or a hematopoietic stem cell marker; or
(b) uptake of acetylated low density lipoprotein (acLDL).

5. The method of claim 4 wherein the hemogenic endothelial cell marker or the hematopoietic stem cell marker is a marker selected from the group consisting of: CD31, CD34, $CD38^{lo/-}$, CD41, CD43, CD45, CD49f, Thy1/CD90, CD105, CD117/c-kit, CD133, CD150, Sca-1, Tie2, VE-Cadherin, KDR/FLK1, Flk-2/Flt3, and CXCR4.

6. The method of claim 5, wherein the hematopoietic stem cell marker is selected from the group consisting of: CD31, CD34, CD41, CD117/c-kit, CD133, Sca-1, Tie2, VE-Cadherin, and CD150.

7. The method of claim 2 further comprising the step of screening the hematopoietic stem cell for a lack of expression of a differentiated hematopoietic lineage (lin) marker.

8. The method of claim 7, wherein the lin⁻ marker is selected from the group consisting of CD4, CD5, CD8, CD45RA/B220, Gr-1/Ly-6G/C, and Ter119.

9. The method of claim 4 further comprising the step of isolating the cell expressing the hematopoietic stem cell marker.

10. The method of claim 9 further comprising the step of co-culturing the hematopoietic stem cell with a stromal cell.

11. The method of claim 10, wherein the stromal cell is an AFT024 stromal cell.

12. The method of claim 2, wherein the combination of transcription factors further comprises a transcription factor selected from the group consisting of stem cell leukemia (SCL/TAL1), runt-related transcription factor 1 (RUNX1), and B lymphoma Mo-MLV insertion region 1 homolog (BMI1).

13. The method of claim 2 further comprising the step of screening the hematopoietic stem cell for:
(a) expression of a hemogenic endothelial cell marker or a hematopoietic stem cell marker; or
(b) uptake of acetylated low density lipoprotein (acLDL).

14. The method of claim 13, wherein the hemogenic endothelial cell marker or the hematopoietic stem cell marker is a marker selected from the group consisting of: CD31, CD34, $CD38^{lo/-}$, CD41, CD43, CD45, CD49f, Thy1/CD90, CD105, CD117/c-kit, CD133, CD150, Sca-1, Tie2, VE-Cadherin, KDR/FLK1, Flk-2/Flt3, and CXCR4.

15. The method of claim 14, wherein the hematopoietic stem cell marker is selected from the group consisting of: CD31, CD34, CD41, CD117/c-kit, CD133, Sca-1, Tie2, VE-Cadherin, and CD150.

16. The method of claim 3 further comprising the step of screening the hematopoietic stem cell for:
   (a) expression of a hemogenic endothelial cell marker or a hematopoietic stem cell marker; or
   (b) uptake of acetylated low density lipoprotein (acLDL).

17. The method of claim 12 further comprising the step of screening the hematopoietic stem cell for:
   (a) expression of a hemogenic endothelial cell marker or a hematopoietic stem cell marker; or
   (b) uptake of acetylated low density lipoprotein (acLDL).

18. The method of claim 1 further comprising the step of screening the hematopoietic stem cell for a lack of expression of a differentiated hematopoietic lineage (lin) marker.

19. The method of claim 18, wherein the lin$^-$ marker is selected from the group consisting of CD4, CD5, CD8, CD45RA/B220, Gr-1/Ly-6G/C, and Ter119.

20. The method of claim 13 further comprising the step of isolating the cell expressing the hematopoietic stem cell marker.

21. The method of claim 20 further comprising the step of co-culturing the hematopoietic stem cell with a stromal cell.

22. The method of claim 21, wherein the stromal cell is an AFT024 stromal cell.

\* \* \* \* \*

SEQUENCE LISTING

```
<160> NUMBER OF SEQ ID NOS: 229

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
agctgaccct gaagttcatc tg                                                22

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
gttgcagata tagtaccggc tg                                                22

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
agaagagatg aggtgtgagg at                                                22

<210> SEQ ID NO 4
<211> LENGTH: 23
<212> TYPE: DNA
<213> ORGANISM: Artificial Sequence
```

```
<220> FEATURE:
<223> OTHER INFORMATION: Synthetic primer

<400> SEQUENCE: 4
atgtacgagt aagaacacct agg                                          23

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
gacggcatcg cagcttggat acac                                         24

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
gctctggttc agcaacatct                                              20

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gacggcatcg cagcttggat acac                                         24

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ctggccgaga gcggttcagg                                              20

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
gacggcatcg cagcttggat acac                                         24

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcgagccact tcatctggat                                              20
```

```
<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
gacggcatcg cagcttggat acac                                           24

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
cagcaacttt cttctaaagt                                                20

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
gacggcatcg cagcttggat acac                                           24

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ctctttaaag cgtcattgac                                                20

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
gacggcatcg cagcttggat acac                                           24

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
caagtccagc tcactatggc                                                20

<210> SEQ ID NO 17
<211> LENGTH: 24
<212> TYPE: DNA
<213> ORGANISM: Artificial Sequence
<220> FEATURE:
<223> OTHER INFORMATION: Synthetic primer
```

<400> SEQUENCE: 17
gacggcatcg cagcttggat acac                    24

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
cggcccttta agtccctcgc                         20

<210> SEQ ID NO 19
<211> LENGTH: 24
<212> TYPE: DNA
<213> ORGANISM: Artificial Sequence
<220> FEATURE:
<223> OTHER INFORMATION: Synthetic primer

<400> SEQUENCE: 19
gacggcatcg cagcttggat acac                    24

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
gtggtgctag ggtcaggaga                         20

<210> SEQ ID NO 21
<211> LENGTH: 24
<212> TYPE: DNA
<213> ORGANISM: Artificial Sequence
<220> FEATURE:
<223> OTHER INFORMATION: Synthetic primer

<400> SEQUENCE: 21
gacggcatcg cagcttggat acac                    24

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
gctgtcggtg cgcactagc                          19

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
gacggcatcg cagcttggat acac                    24

<210> SEQ ID NO 24

-continued

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
gatggggcca cggaggagac                                                     20

<210> SEQ ID NO 25
<211> LENGTH: 24
<212> TYPE: DNA
<213> ORGANISM: Artificial Sequence
<220> FEATURE:
<223> OTHER INFORMATION: Synthetic primer

<400> SEQUENCE: 25
gacggcatcg cagcttggat acac                                                24

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
caggagggcc ttgccattca                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
gaggcaccac tgaaccctaa                                                     20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tacatggcgg ggacattgaa                                                     20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
ccctaaggcc aaccgtgaaa                                                     20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
```
cagcctggat ggctacgtac                                          20

<210> SEQ ID NO 31
<211> LENGTH: 19
<212> TYPE: DNA
<213> ORGANISM: Artificial Sequence
<220> FEATURE:
<223> OTHER INFORMATION: Synthetic primer

<400> SEQUENCE: 31
gactacgccg caagggata                                           19

<210> SEQ ID NO 32
<211> LENGTH: 21
<212> TYPE: DNA
<213> ORGANISM: Artificial Sequence
<220> FEATURE:
<223> OTHER INFORMATION: Synthetic primer

<400> SEQUENCE: 32
gcatcctgtg gcttttcttc c                                        21

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
cctgtgtgga gggtacttca                                          20

<210> SEQ ID NO 34
<211> LENGTH: 21
<212> TYPE: DNA
<213> ORGANISM: Artificial Sequence
<220> FEATURE:
<223> OTHER INFORMATION: Synthetic primer

<400> SEQUENCE: 34
tgctggtctc caagtaacgt a                                        21

<210> SEQ ID NO 35
<211> LENGTH: 19
<212> TYPE: DNA
<213> ORGANISM: Artificial Sequence
<220> FEATURE:
<223> OTHER INFORMATION: Synthetic primer

<400> SEQUENCE: 35
gaaccgggct tgagtaccc                                           19

<210> SEQ ID NO 36
<211> LENGTH: 19
<212> TYPE: DNA
<213> ORGANISM: Artificial Sequence
<220> FEATURE:
<223> OTHER INFORMATION: Synthetic primer

<400> SEQUENCE: 36
ggtccctggg atgttctcc                                           19

<210> SEQ ID NO 37
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 37
tctttcactg ggctgaagca                                                    20

<210> SEQ ID NO 38
<211> LENGTH: 22
<212> TYPE: DNA
<213> ORGANISM: Artificial Sequence
<220> FEATURE:
<223> OTHER INFORMATION: Synthetic primer

<400> SEQUENCE: 38
ggttcctatc cagcctgttg ta                                                 22

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
ccgagccata tgcttacaca                                                    20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
acctcacttc tcggattcca                                                    20

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
acagctattc ctgggttcca                                                    20

<210> SEQ ID NO 42
<211> LENGTH: 21
<212> TYPE: DNA
<213> ORGANISM: Artificial Sequence
<220> FEATURE:
<223> OTHER INFORMATION: Synthetic primer

<400> SEQUENCE: 42
agctgtctct aaggccacat a                                                  21

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
aacgaggaca gcaacttcac                                                    20
```

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
tggcatgctc ccgattaaac                                            20

<210> SEQ ID NO 45
<211> LENGTH: 21
<212> TYPE: DNA
<213> ORGANISM: Artificial Sequence
<220> FEATURE:
<223> OTHER INFORMATION: Synthetic primer

<400> SEQUENCE: 45
gaacatctca gggccgaaaa c                                          21

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
tctgcgcttg gagtgataga a                                          21

<210> SEQ ID NO 47
<211> LENGTH: 20
<212> TYPE: DNA
<213> ORGANISM: Artificial Sequence
<220> FEATURE:
<223> OTHER INFORMATION: Synthetic primer

<400> SEQUENCE: 47
cagtgtccag ggatgaggaa                                            20

<210> SEQ ID NO 48
<211> LENGTH: 19
<212> TYPE: DNA
<213> ORGANISM: Artificial Sequence
<220> FEATURE:
<223> OTHER INFORMATION: Synthetic primer

<400> SEQUENCE: 48
ttcggggaac cgtctgaaa                                             19

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
ctttgtgtac cgctgggaac                                            20

<210> SEQ ID NO 50
<211> LENGTH: 16
<212> TYPE: DNA
<213> ORGANISM: Artificial Sequence
<220> FEATURE:

<223> OTHER INFORMATION: Synthetic primer

<400> SEQUENCE: 50
tggccgcgaa gttcca                                                   16

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
ctgaaccgct ttggcaagac                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
ccttgcttca ggagctccaa                                               20

<210> SEQ ID NO 53
<211> LENGTH: 19
<212> TYPE: DNA
<213> ORGANISM: Artificial Sequence
<220> FEATURE:
<223> OTHER INFORMATION: Synthetic primer

<400> SEQUENCE: 53
atggcagtgt gcacgtcta                                                19

<210> SEQ ID NO 54
<211> LENGTH: 22
<212> TYPE: DNA
<213> ORGANISM: Artificial Sequence
<220> FEATURE:
<223> OTHER INFORMATION: Synthetic primer

<400> SEQUENCE: 54
tggcaagaat cagagcaaaa cc                                            22

<210> SEQ ID NO 55
<211> LENGTH: 21
<212> TYPE: DNA
<213> ORGANISM: Artificial Sequence
<220> FEATURE:
<223> OTHER INFORMATION: Synthetic primer

<400> SEQUENCE: 55
tgctggaaag aatggggaga c                                             21

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
ggtccagaat ctcccttgtc ac                                            22

```
<210> SEQ ID NO 57
<211> LENGTH: 22
<212> TYPE: DNA
<213> ORGANISM: Artificial Sequence
<220> FEATURE:
<223> OTHER INFORMATION: Synthetic primer

<400> SEQUENCE: 57
ttccagggtc tgatggttta cc                                              22

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
tcctttaggc cccgaagaac                                                 20

<210> SEQ ID NO 59
<211> LENGTH: 22
<212> TYPE: DNA
<213> ORGANISM: Artificial Sequence
<220> FEATURE:
<223> OTHER INFORMATION: Synthetic primer

<400> SEQUENCE: 59
gactggctag ggacatcatg aa                                              22

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
tctggggcca tccactttac                                                 20

<210> SEQ ID NO 61
<211> LENGTH: 18
<212> TYPE: DNA
<213> ORGANISM: Artificial Sequence
<220> FEATURE:
<223> OTHER INFORMATION: Synthetic primer

<400> SEQUENCE: 61
cgacgtggtg gctacgaa                                                   18

<210> SEQ ID NO 62
<211> LENGTH: 21
<212> TYPE: DNA
<213> ORGANISM: Artificial Sequence
<220> FEATURE:
<223> OTHER INFORMATION: Synthetic primer

<400> SEQUENCE: 62
ggtgcagtgg gaagagttac a                                               21

<210> SEQ ID NO 63
<211> LENGTH: 19
<212> TYPE: DNA
<213> ORGANISM: Artificial Sequence
<220> FEATURE:
<223> OTHER INFORMATION: Synthetic primer
```

<400> SEQUENCE: 63
gcgtccaact cctggatca                                                19

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
gaggtgcatg aggcaggata                                               20

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
agccattggc ctggagatta                                               20

<210> SEQ ID NO 66
<211> LENGTH: 21
<212> TYPE: DNA
<213> ORGANISM: Artificial Sequence
<220> FEATURE:
<223> OTHER INFORMATION: Synthetic primer

<400> SEQUENCE: 66
gcagcctcct cttttgcttt a                                             21

<210> SEQ ID NO 67
<211> LENGTH: 19
<212> TYPE: DNA
<213> ORGANISM: Artificial Sequence
<220> FEATURE:
<223> OTHER INFORMATION: Synthetic primer

<400> SEQUENCE: 67
cgccagaagt gcagaaaca                                                19

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
aatgaagagt gggtgctcca                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
gacgtccgga aaatcaccaa                                               20

<210> SEQ ID NO 70
<211> LENGTH: 20

```
<212> TYPE: DNA
<213> ORGANISM: Artificial Sequence
<220> FEATURE:
<223> OTHER INFORMATION: Synthetic primer

<400> SEQUENCE: 70
gatcattgca tgggcttcca                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic primer

<400> SEQUENCE: 71
tggaagggca cagagatgaa                                               20

<210> SEQ ID NO 72
<211> LENGTH: 22
<212> TYPE: DNA
<213> ORGANISM: Artificial Sequence
<220> FEATURE:
<223> OTHER INFORMATION: Synthetic primer

<400> SEQUENCE: 72
agagtgatcc ataccacagg ac                                            22

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
acaaccctat gagcacctga c                                             21

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
ggctgggata actcgtctcc                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic primer

<400> SEQUENCE: 75
ttgcaaccac tccatcaacc                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic primer

<400> SEQUENCE: 76
```
taacaaccag cgcgataacc                        20

<210> SEQ ID NO 77
<211> LENGTH: 19
<212> TYPE: DNA
<213> ORGANISM: Artificial Sequence
<220> FEATURE:
<223> OTHER INFORMATION: Synthetic primer

<400> SEQUENCE: 77
tcacccacga aagcacaca                         19

<210> SEQ ID NO 78
<211> LENGTH: 19
<212> TYPE: DNA
<213> ORGANISM: Artificial Sequence
<220> FEATURE:
<223> OTHER INFORMATION: Synthetic primer

<400> SEQUENCE: 78
ctgtggggat ggcagagac                         19

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
acggttaatg catgccagaa                        20

<210> SEQ ID NO 80
<211> LENGTH: 22
<212> TYPE: DNA
<213> ORGANISM: Artificial Sequence
<220> FEATURE:
<223> OTHER INFORMATION: Synthetic primer

<400> SEQUENCE: 80
tttgcgtagc ttcgggatat ac                     22

<210> SEQ ID NO 81
<211> LENGTH: 20
<212> TYPE: DNA
<213> ORGANISM: Artificial Sequence
<220> FEATURE:
<223> OTHER INFORMATION: Synthetic primer

<400> SEQUENCE: 81
ccctccaaat cgaacaagca                        20

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
gaggaattgc cacagctgaa                        20

<210> SEQ ID NO 83
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 83
aggctgtagc atcgtggaaa                                              20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
ttgtaggccc aatccggaaa                                              20

<210> SEQ ID NO 85
<211> LENGTH: 21
<212> TYPE: DNA
<213> ORGANISM: Artificial Sequence
<220> FEATURE:
<223> OTHER INFORMATION: Synthetic primer

<400> SEQUENCE: 85
gccatgccca ttgggagaat a                                            21

<210> SEQ ID NO 86
<211> LENGTH: 21
<212> TYPE: DNA
<213> ORGANISM: Artificial Sequence
<220> FEATURE:
<223> OTHER INFORMATION: Synthetic primer

<400> SEQUENCE: 86
aagttttcgt accggctgtc a                                            21

<210> SEQ ID NO 87
<211> LENGTH: 22
<212> TYPE: DNA
<213> ORGANISM: Artificial Sequence
<220> FEATURE:
<223> OTHER INFORMATION: Synthetic primer

<400> SEQUENCE: 87
tgatggaaaa gtgcatggtg ac                                           22

<210> SEQ ID NO 88
<211> LENGTH: 23
<212> TYPE: DNA
<213> ORGANISM: Artificial Sequence
<220> FEATURE:
<223> OTHER INFORMATION: Synthetic primer

<400> SEQUENCE: 88
gaccaagagc atttaccaac tcc                                          23

<210> SEQ ID NO 89
<211> LENGTH: 20
<212> TYPE: DNA
<213> ORGANISM: Artificial Sequence
<220> FEATURE:
<223> OTHER INFORMATION: Synthetic primer

<400> SEQUENCE: 89
tgagacatgc cctcctgtaa                                              20
```

<210> SEQ ID NO 90
<211> LENGTH: 20
<212> TYPE: DNA
<213> ORGANISM: Artificial Sequence
<220> FEATURE:
<223> OTHER INFORMATION: Synthetic primer

<400> SEQUENCE: 90
tgtgatgggg ttgggtctaa                                            20

<210> SEQ ID NO 91
<211> LENGTH: 21
<212> TYPE: DNA
<213> ORGANISM: Artificial Sequence
<220> FEATURE:
<223> OTHER INFORMATION: Synthetic primer

<400> SEQUENCE: 91
tctccttgga ggatcacaga c                                          21

<210> SEQ ID NO 92
<211> LENGTH: 20
<212> TYPE: DNA
<213> ORGANISM: Artificial Sequence
<220> FEATURE:
<223> OTHER INFORMATION: Synthetic primer

<400> SEQUENCE: 92
ttggccccag gatctgataa                                            20

<210> SEQ ID NO 93
<211> LENGTH: 20
<212> TYPE: DNA
<213> ORGANISM: Artificial Sequence
<220> FEATURE:
<223> OTHER INFORMATION: Synthetic primer

<400> SEQUENCE: 93
ccttccccaa cctgacttca                                            20

<210> SEQ ID NO 94
<211> LENGTH: 22
<212> TYPE: DNA
<213> ORGANISM: Artificial Sequence
<220> FEATURE:
<223> OTHER INFORMATION: Synthetic primer

<400> SEQUENCE: 94
gttgccaccc atgttctgat ac                                         22

<210> SEQ ID NO 95
<211> LENGTH: 22
<212> TYPE: DNA
<213> ORGANISM: Artificial Sequence
<220> FEATURE:
<223> OTHER INFORMATION: Synthetic primer

<400> SEQUENCE: 95
gtcccatctc ctccaacttc aa                                         22

<210> SEQ ID NO 96
<211> LENGTH: 19
<212> TYPE: DNA
<213> ORGANISM: Artificial Sequence
<220> FEATURE:
<223> OTHER INFORMATION: Synthetic primer

<400> SEQUENCE: 96
ggccacagtg actgggtaa                                                19

<210> SEQ ID NO 97
<211> LENGTH: 20
<212> TYPE: DNA
<213> ORGANISM: Artificial Sequence
<220> FEATURE:
<223> OTHER INFORMATION: Synthetic primer

<400> SEQUENCE: 97
cgtcattgcc ctgaagaaca                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic primer

<400> SEQUENCE: 98
aagggtaacc agttggggaa                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic primer

<400> SEQUENCE: 99
atgggctctc ctgtcaacac                                               20

<210> SEQ ID NO 100
<211> LENGTH: 19
<212> TYPE: DNA
<213> ORGANISM: Artificial Sequence
<220> FEATURE:
<223> OTHER INFORMATION: Synthetic primer

<400> SEQUENCE: 100
gctgtcaccg tggggataa                                                19

<210> SEQ ID NO 101
<211> LENGTH: 20
<212> TYPE: DNA
<213> ORGANISM: Artificial Sequence
<220> FEATURE:
<223> OTHER INFORMATION: Synthetic primer

<400> SEQUENCE: 101
gttcctcaag tgcctcaacc                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
tgcataggtt tcgtcctcca                                               20

<210> SEQ ID NO 103

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 103
cacccctaag cagagaagca a                                              21

<210> SEQ ID NO 104
<211> LENGTH: 19
<212> TYPE: DNA
<213> ORGANISM: Artificial Sequence
<220> FEATURE:
<223> OTHER INFORMATION: Synthetic primer

<400> SEQUENCE: 104
tgtggcacca cagttgaca                                                 19

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
cctaccgggt tcggatgtaa                                                20

<210> SEQ ID NO 106
<211> LENGTH: 18
<212> TYPE: DNA
<213> ORGANISM: Artificial Sequence
<220> FEATURE:
<223> OTHER INFORMATION: Synthetic primer

<400> SEQUENCE: 106
ccgcagttca cacactcc                                                  18

<210> SEQ ID NO 107
<211> LENGTH: 18
<212> TYPE: DNA
<213> ORGANISM: Artificial Sequence
<220> FEATURE:
<223> OTHER INFORMATION: Synthetic primer

<400> SEQUENCE: 107
tgagcctgga gcaacaca                                                  18

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
agcgtggatg acctcttgaa                                                20

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
```

```
ccaggcatgg acacttacca                                           20

<210> SEQ ID NO 110
<211> LENGTH: 19
<212> TYPE: DNA
<213> ORGANISM: Artificial Sequence
<220> FEATURE:
<223> OTHER INFORMATION: Synthetic primer

<400> SEQUENCE: 110
cggcggacat gcacttcta                                            19

<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111
gcggcaagga gtttgtagaa                                           20

<210> SEQ ID NO 112
<211> LENGTH: 19
<212> TYPE: DNA
<213> ORGANISM: Artificial Sequence
<220> FEATURE:
<223> OTHER INFORMATION: Synthetic primer

<400> SEQUENCE: 112
gccatggcct gcactaata                                            19

<210> SEQ ID NO 113
<211> LENGTH: 20
<212> TYPE: DNA
<213> ORGANISM: Artificial Sequence
<220> FEATURE:
<223> OTHER INFORMATION: Synthetic primer

<400> SEQUENCE: 113
ctctccccac ccgagagaaa                                           20

<210> SEQ ID NO 114
<211> LENGTH: 21
<212> TYPE: DNA
<213> ORGANISM: Artificial Sequence
<220> FEATURE:
<223> OTHER INFORMATION: Synthetic primer

<400> SEQUENCE: 114
tagctcggcg attctgaaac c                                         21

<210> SEQ ID NO 115
<211> LENGTH: 21
<212> TYPE: DNA
<213> ORGANISM: Artificial Sequence
<220> FEATURE:
<223> OTHER INFORMATION: Synthetic primer

<400> SEQUENCE: 115
tgaagccaca gcccatgatt a                                         21

<210> SEQ ID NO 116
<211> LENGTH: 19
<212> TYPE: DNA
```

<213> ORGANISM: Artificial Sequence
<220> FEATURE:
<223> OTHER INFORMATION: Synthetic primer

<400> SEQUENCE: 116
cctcgcccag tacttgtca                                                    19

<210> SEQ ID NO 117
<211> LENGTH: 22
<212> TYPE: DNA
<213> ORGANISM: Artificial Sequence
<220> FEATURE:
<223> OTHER INFORMATION: Synthetic primer

<400> SEQUENCE: 117
agtcaaggca gaacactaag ca                                                22

<210> SEQ ID NO 118
<211> LENGTH: 17
<212> TYPE: DNA
<213> ORGANISM: Artificial Sequence
<220> FEATURE:
<223> OTHER INFORMATION: Synthetic primer

<400> SEQUENCE: 118
caggcgggct cttgtca                                                      17

<210> SEQ ID NO 119
<211> LENGTH: 21
<212> TYPE: DNA
<213> ORGANISM: Artificial Sequence
<220> FEATURE:
<223> OTHER INFORMATION: Synthetic primer

<400> SEQUENCE: 119
ctccgaaaac aatgccgaga a                                                 21

<210> SEQ ID NO 120
<211> LENGTH: 19
<212> TYPE: DNA
<213> ORGANISM: Artificial Sequence
<220> FEATURE:
<223> OTHER INFORMATION: Synthetic primer

<400> SEQUENCE: 120
cgagtggagc gagcatgta                                                    19

<210> SEQ ID NO 121
<211> LENGTH: 19
<212> TYPE: DNA
<213> ORGANISM: Artificial Sequence
<220> FEATURE:
<223> OTHER INFORMATION: Synthetic primer

<400> SEQUENCE: 121
cctggatgcg caaagttca                                                    19

<210> SEQ ID NO 122
<211> LENGTH: 18
<212> TYPE: DNA
<213> ORGANISM: Artificial Sequence
<220> FEATURE:
<223> OTHER INFORMATION: Synthetic primer

<400> SEQUENCE: 122
gacctgctgg cgagtgta                                                     18

```
<210> SEQ ID NO 123
<211> LENGTH: 22
<212> TYPE: DNA
<213> ORGANISM: Artificial Sequence
<220> FEATURE:
<223> OTHER INFORMATION: Synthetic primer

<400> SEQUENCE: 123
cagtacagcc ccaaaatggt ta                                              22

<210> SEQ ID NO 124
<211> LENGTH: 20
<212> TYPE: DNA
<213> ORGANISM: Artificial Sequence
<220> FEATURE:
<223> OTHER INFORMATION: Synthetic primer

<400> SEQUENCE: 124
agtctggcct gtatccaaca                                                 20

<210> SEQ ID NO 125
<211> LENGTH: 19
<212> TYPE: DNA
<213> ORGANISM: Artificial Sequence
<220> FEATURE:
<223> OTHER INFORMATION: Synthetic primer

<400> SEQUENCE: 125
accctgaacg gcgagatca                                                  19

<210> SEQ ID NO 126
<211> LENGTH: 19
<212> TYPE: DNA
<213> ORGANISM: Artificial Sequence
<220> FEATURE:
<223> OTHER INFORMATION: Synthetic primer

<400> SEQUENCE: 126
gatcgtcggc tggaacaca                                                  19

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
gcggacaggg aagggttaaa                                                 20

<210> SEQ ID NO 128
<211> LENGTH: 18
<212> TYPE: DNA
<213> ORGANISM: Artificial Sequence
<220> FEATURE:
<223> OTHER INFORMATION: Synthetic primer

<400> SEQUENCE: 128
ccaggaccag gcgacaaa                                                   18

<210> SEQ ID NO 129
<211> LENGTH: 18
<212> TYPE: DNA
<213> ORGANISM: Artificial Sequence
<220> FEATURE:
```

<223> OTHER INFORMATION: Synthetic primer

<400> SEQUENCE: 129
ctgtgcccac ccattcca                                                          18

<210> SEQ ID NO 130
<211> LENGTH: 21
<212> TYPE: DNA
<213> ORGANISM: Artificial Sequence
<220> FEATURE:
<223> OTHER INFORMATION: Synthetic primer

<400> SEQUENCE: 130
agtcttcaag agctggttcc c                                                      21

<210> SEQ ID NO 131
<211> LENGTH: 19
<212> TYPE: DNA
<213> ORGANISM: Artificial Sequence
<220> FEATURE:
<223> OTHER INFORMATION: Synthetic primer

<400> SEQUENCE: 131
gcaggaatcc tctggaacc                                                         19

<210> SEQ ID NO 132
<211> LENGTH: 20
<212> TYPE: DNA
<213> ORGANISM: Artificial Sequence
<220> FEATURE:
<223> OTHER INFORMATION: Synthetic primer

<400> SEQUENCE: 132
ggacactcgt tgcttctgta                                                        20

<210> SEQ ID NO 133
<211> LENGTH: 20
<212> TYPE: DNA
<213> ORGANISM: Artificial Sequence
<220> FEATURE:
<223> OTHER INFORMATION: Synthetic primer

<400> SEQUENCE: 133
tggcagtcac tgacgtcaac                                                        20

<210> SEQ ID NO 134
<211> LENGTH: 23
<212> TYPE: DNA
<213> ORGANISM: Artificial Sequence
<220> FEATURE:
<223> OTHER INFORMATION: Synthetic primer

<400> SEQUENCE: 134
tctgccctgc tctccatata caa                                                    23

<210> SEQ ID NO 135
<211> LENGTH: 20
<212> TYPE: DNA
<213> ORGANISM: Artificial Sequence
<220> FEATURE:
<223> OTHER INFORMATION: Synthetic primer

<400> SEQUENCE: 135
aagcagctga atgggaggac                                                        20

```
<210> SEQ ID NO 136
<211> LENGTH: 22
<212> TYPE: DNA
<213> ORGANISM: Artificial Sequence
<220> FEATURE:
<223> OTHER INFORMATION: Synthetic primer

<400> SEQUENCE: 136
gccccattgg ttttgtgaaa ca                                              22

<210> SEQ ID NO 137
<211> LENGTH: 22
<212> TYPE: DNA
<213> ORGANISM: Artificial Sequence
<220> FEATURE:
<223> OTHER INFORMATION: Synthetic primer

<400> SEQUENCE: 137
ggaaacgacc ttctacgacg at                                              22

<210> SEQ ID NO 138
<211> LENGTH: 20
<212> TYPE: DNA
<213> ORGANISM: Artificial Sequence
<220> FEATURE:
<223> OTHER INFORMATION: Synthetic primer

<400> SEQUENCE: 138
gggttactgt agccgtaggc                                                 20

<210> SEQ ID NO 139
<211> LENGTH: 20
<212> TYPE: DNA
<213> ORGANISM: Artificial Sequence
<220> FEATURE:
<223> OTHER INFORMATION: Synthetic primer

<400> SEQUENCE: 139
atttcacctg gcactctcca                                                 20

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
tcccaggaaa gggtttcaca                                                 20

<210> SEQ ID NO 141
<211> LENGTH: 20
<212> TYPE: DNA
<213> ORGANISM: Artificial Sequence
<220> FEATURE:
<223> OTHER INFORMATION: Synthetic primer

<400> SEQUENCE: 141
gtgccaacca agacagacaa                                                 20

<210> SEQ ID NO 142
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 142
ttccatgatg gcaggagtca                                               20

<210> SEQ ID NO 143
<211> LENGTH: 21
<212> TYPE: DNA
<213> ORGANISM: Artificial Sequence
<220> FEATURE:
<223> OTHER INFORMATION: Synthetic primer

<400> SEQUENCE: 143
gcgggaatcc tgtgactgat a                                             21

<210> SEQ ID NO 144
<211> LENGTH: 21
<212> TYPE: DNA
<213> ORGANISM: Artificial Sequence
<220> FEATURE:
<223> OTHER INFORMATION: Synthetic primer

<400> SEQUENCE: 144
cggcgacata gttgagggtt a                                             21

<210> SEQ ID NO 145
<211> LENGTH: 22
<212> TYPE: DNA
<213> ORGANISM: Artificial Sequence
<220> FEATURE:
<223> OTHER INFORMATION: Synthetic primer

<400> SEQUENCE: 145
ctactacaag ctgggacgga aa                                            22

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
tcacaggatg cacagagacc                                               20

<210> SEQ ID NO 147
<211> LENGTH: 22
<212> TYPE: DNA
<213> ORGANISM: Artificial Sequence
<220> FEATURE:
<223> OTHER INFORMATION: Synthetic primer

<400> SEQUENCE: 147
accctgatgg agtctgtgtt ac                                            22

<210> SEQ ID NO 148
<211> LENGTH: 20
<212> TYPE: DNA
<213> ORGANISM: Artificial Sequence
<220> FEATURE:
<223> OTHER INFORMATION: Synthetic primer

<400> SEQUENCE: 148
agggcagatg ggtaagcaaa                                               20

<210> SEQ ID NO 149
<211> LENGTH: 19

```
<212> TYPE: DNA
<213> ORGANISM: Artificial Sequence
<220> FEATURE:
<223> OTHER INFORMATION: Synthetic primer

<400> SEQUENCE: 149
aagcgcagac caagccata                                                  19

<210> SEQ ID NO 150
<211> LENGTH: 19
<212> TYPE: DNA
<213> ORGANISM: Artificial Sequence
<220> FEATURE:
<223> OTHER INFORMATION: Synthetic primer

<400> SEQUENCE: 150
tcacggctgt tggtgaaca                                                  19

<210> SEQ ID NO 151
<211> LENGTH: 22
<212> TYPE: DNA
<213> ORGANISM: Artificial Sequence
<220> FEATURE:
<223> OTHER INFORMATION: Synthetic primer

<400> SEQUENCE: 151
caggacggac atttcgatac ac                                              22

<210> SEQ ID NO 152
<211> LENGTH: 22
<212> TYPE: DNA
<213> ORGANISM: Artificial Sequence
<220> FEATURE:
<223> OTHER INFORMATION: Synthetic primer

<400> SEQUENCE: 152
accattctcc actctggtct ac                                              22

<210> SEQ ID NO 153
<211> LENGTH: 21
<212> TYPE: DNA
<213> ORGANISM: Artificial Sequence
<220> FEATURE:
<223> OTHER INFORMATION: Synthetic primer

<400> SEQUENCE: 153
agttggcaca agatacagga c                                               21

<210> SEQ ID NO 154
<211> LENGTH: 20
<212> TYPE: DNA
<213> ORGANISM: Artificial Sequence
<220> FEATURE:
<223> OTHER INFORMATION: Synthetic primer

<400> SEQUENCE: 154
gggctgcact attcttctcc                                                 20

<210> SEQ ID NO 155
<211> LENGTH: 20
<212> TYPE: DNA
<213> ORGANISM: Artificial Sequence
<220> FEATURE:
<223> OTHER INFORMATION: Synthetic primer

<400> SEQUENCE: 155
```
aacagactga ccagcccaaa                                               20

<210> SEQ ID NO 156
<211> LENGTH: 21
<212> TYPE: DNA
<213> ORGANISM: Artificial Sequence
<220> FEATURE:
<223> OTHER INFORMATION: Synthetic primer

<400> SEQUENCE: 156
tttaatccgg ggtcctcgaa c                                             21

<210> SEQ ID NO 157
<211> LENGTH: 21
<212> TYPE: DNA
<213> ORGANISM: Artificial Sequence
<220> FEATURE:
<223> OTHER INFORMATION: Synthetic primer

<400> SEQUENCE: 157
tgactcggag atggaaagac c                                             21

<210> SEQ ID NO 158
<211> LENGTH: 19
<212> TYPE: DNA
<213> ORGANISM: Artificial Sequence
<220> FEATURE:
<223> OTHER INFORMATION: Synthetic primer

<400> SEQUENCE: 158
tgtcactgcc gtcactcaa                                                19

<210> SEQ ID NO 159
<211> LENGTH: 20
<212> TYPE: DNA
<213> ORGANISM: Artificial Sequence
<220> FEATURE:
<223> OTHER INFORMATION: Synthetic primer

<400> SEQUENCE: 159
agctcaagag acctgctacc                                               20

<210> SEQ ID NO 160
<211> LENGTH: 18
<212> TYPE: DNA
<213> ORGANISM: Artificial Sequence
<220> FEATURE:
<223> OTHER INFORMATION: Synthetic primer

<400> SEQUENCE: 160
caccgagaga tggctcca                                                 18

<210> SEQ ID NO 161
<211> LENGTH: 20
<212> TYPE: DNA
<213> ORGANISM: Artificial Sequence
<220> FEATURE:
<223> OTHER INFORMATION: Synthetic primer

<400> SEQUENCE: 161
tcctccgtca acagcgaata                                               20

<210> SEQ ID NO 162
<211> LENGTH: 21
<212> TYPE: DNA
<213> ORGANISM: Artificial Sequence

```
<220> FEATURE:
<223> OTHER INFORMATION: Synthetic primer

<400> SEQUENCE: 162
caatgcgaca ggatagggaa c                                              21

<210> SEQ ID NO 163
<211> LENGTH: 19
<212> TYPE: DNA
<213> ORGANISM: Artificial Sequence
<220> FEATURE:
<223> OTHER INFORMATION: Synthetic primer

<400> SEQUENCE: 163
agtgctgcat gaggagaca                                                 19

<210> SEQ ID NO 164
<211> LENGTH: 21
<212> TYPE: DNA
<213> ORGANISM: Artificial Sequence
<220> FEATURE:
<223> OTHER INFORMATION: Synthetic primer

<400> SEQUENCE: 164
tctccacaga caccacatca a                                              21

<210> SEQ ID NO 165
<211> LENGTH: 20
<212> TYPE: DNA
<213> ORGANISM: Artificial Sequence
<220> FEATURE:
<223> OTHER INFORMATION: Synthetic primer

<400> SEQUENCE: 165
cctcctcagc agaacaggaa                                                20

<210> SEQ ID NO 166
<211> LENGTH: 22
<212> TYPE: DNA
<213> ORGANISM: Artificial Sequence
<220> FEATURE:
<223> OTHER INFORMATION: Synthetic primer

<400> SEQUENCE: 166
tgaggctcaa aagatgtctc ac                                             22

<210> SEQ ID NO 167
<211> LENGTH: 22
<212> TYPE: DNA
<213> ORGANISM: Artificial Sequence
<220> FEATURE:
<223> OTHER INFORMATION: Synthetic primer

<400> SEQUENCE: 167
gggattctgg caagacagac ta                                             22

<210> SEQ ID NO 168
<211> LENGTH: 20
<212> TYPE: DNA
<213> ORGANISM: Artificial Sequence
<220> FEATURE:
<223> OTHER INFORMATION: Synthetic primer

<400> SEQUENCE: 168
gcagccaaac accaaagtca                                                20
```

```
<210> SEQ ID NO 169
<211> LENGTH: 20
<212> TYPE: DNA
<213> ORGANISM: Artificial Sequence
<220> FEATURE:
<223> OTHER INFORMATION: Synthetic primer

<400> SEQUENCE: 169
gcacagtgat gctgaacaac                                                   20

<210> SEQ ID NO 170
<211> LENGTH: 20
<212> TYPE: DNA
<213> ORGANISM: Artificial Sequence
<220> FEATURE:
<223> OTHER INFORMATION: Synthetic primer

<400> SEQUENCE: 170
gtcaccttgg gcttggatac                                                   20

<210> SEQ ID NO 171
<211> LENGTH: 21
<212> TYPE: DNA
<213> ORGANISM: Artificial Sequence
<220> FEATURE:
<223> OTHER INFORMATION: Synthetic primer

<400> SEQUENCE: 171
tccctacagc agatcactca c                                                 21

<210> SEQ ID NO 172
<211> LENGTH: 20
<212> TYPE: DNA
<213> ORGANISM: Artificial Sequence
<220> FEATURE:
<223> OTHER INFORMATION: Synthetic primer

<400> SEQUENCE: 172
cgccggttac agaaccatac                                                   20

<210> SEQ ID NO 173
<211> LENGTH: 20
<212> TYPE: DNA
<213> ORGANISM: Artificial Sequence
<220> FEATURE:
<223> OTHER INFORMATION: Synthetic primer

<400> SEQUENCE: 173
tccgaaactt catcgccaac                                                   20

<210> SEQ ID NO 174
<211> LENGTH: 21
<212> TYPE: DNA
<213> ORGANISM: Artificial Sequence
<220> FEATURE:
<223> OTHER INFORMATION: Synthetic primer

<400> SEQUENCE: 174
ctgtccaggt cttggatctc a                                                 21

<210> SEQ ID NO 175
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 175
gcgatggact ctgctgttaa                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic primer

<400> SEQUENCE: 176
cctatgccga accagaacaa                                              20

<210> SEQ ID NO 177
<211> LENGTH: 22
<212> TYPE: DNA
<213> ORGANISM: Artificial Sequence
<220> FEATURE:
<223> OTHER INFORMATION: Synthetic primer

<400> SEQUENCE: 177
gagacattat gacaccgcca aa                                           22

<210> SEQ ID NO 178
<211> LENGTH: 22
<212> TYPE: DNA
<213> ORGANISM: Artificial Sequence
<220> FEATURE:
<223> OTHER INFORMATION: Synthetic primer

<400> SEQUENCE: 178
aagttctagc tgtggtgggt ta                                           22

<210> SEQ ID NO 179
<211> LENGTH: 20
<212> TYPE: DNA
<213> ORGANISM: Artificial Sequence
<220> FEATURE:
<223> OTHER INFORMATION: Synthetic primer

<400> SEQUENCE: 179
tgatgagggc agactgttcc                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic primer

<400> SEQUENCE: 180
tcgggcatct ttgatgggaa                                              20

<210> SEQ ID NO 181
<211> LENGTH: 21
<212> TYPE: DNA
<213> ORGANISM: Artificial Sequence
<220> FEATURE:
<223> OTHER INFORMATION: Synthetic primer

<400> SEQUENCE: 181
agaaccaggt agcgagattc a                                            21

<210> SEQ ID NO 182
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 182
acggtgatgg tcagagtgaa                                               20

<210> SEQ ID NO 183
<211> LENGTH: 21
<212> TYPE: DNA
<213> ORGANISM: Artificial Sequence
<220> FEATURE:
<223> OTHER INFORMATION: Synthetic primer

<400> SEQUENCE: 183
aacagatgca cgtcctcgat a                                             21

<210> SEQ ID NO 184
<211> LENGTH: 19
<212> TYPE: DNA
<213> ORGANISM: Artificial Sequence
<220> FEATURE:
<223> OTHER INFORMATION: Synthetic primer

<400> SEQUENCE: 184
catccggggc atgtaggaa                                                19

<210> SEQ ID NO 185
<211> LENGTH: 21
<212> TYPE: DNA
<213> ORGANISM: Artificial Sequence
<220> FEATURE:
<223> OTHER INFORMATION: Synthetic primer

<400> SEQUENCE: 185
cagaacccag atctgcacaa c                                             21

<210> SEQ ID NO 186
<211> LENGTH: 20
<212> TYPE: DNA
<213> ORGANISM: Artificial Sequence
<220> FEATURE:
<223> OTHER INFORMATION: Synthetic primer

<400> SEQUENCE: 186
gcttctctgc caaggtcaac                                               20

<210> SEQ ID NO 187
<211> LENGTH: 20
<212> TYPE: DNA
<213> ORGANISM: Artificial Sequence
<220> FEATURE:
<223> OTHER INFORMATION: Synthetic primer

<400> SEQUENCE: 187
catgtccctg ggcagtttca                                               20

<210> SEQ ID NO 188
<211> LENGTH: 21
<212> TYPE: DNA
<213> ORGANISM: Artificial Sequence
<220> FEATURE:
<223> OTHER INFORMATION: Synthetic primer

<400> SEQUENCE: 188
```
ctgagccggg ttcgaagtta a            21

<210> SEQ ID NO 189
<211> LENGTH: 20
<212> TYPE: DNA
<213> ORGANISM: Artificial Sequence
<220> FEATURE:
<223> OTHER INFORMATION: Synthetic primer

<400> SEQUENCE: 189
tgaccaagcc tcaggaagaa            20

<210> SEQ ID NO 190
<211> LENGTH: 19
<212> TYPE: DNA
<213> ORGANISM: Artificial Sequence
<220> FEATURE:
<223> OTHER INFORMATION: Synthetic primer

<400> SEQUENCE: 190
gccccaaaga ggaggagaa            19

<210> SEQ ID NO 191
<211> LENGTH: 21
<212> TYPE: DNA
<213> ORGANISM: Artificial Sequence
<220> FEATURE:
<223> OTHER INFORMATION: Synthetic primer

<400> SEQUENCE: 191
ccacagcagg ttcatcttca a            21

<210> SEQ ID NO 192
<211> LENGTH: 20
<212> TYPE: DNA
<213> ORGANISM: Artificial Sequence
<220> FEATURE:
<223> OTHER INFORMATION: Synthetic primer

<400> SEQUENCE: 192
ttcctgcata ggagccatca            20

<210> SEQ ID NO 193
<211> LENGTH: 17
<212> TYPE: DNA
<213> ORGANISM: Artificial Sequence
<220> FEATURE:
<223> OTHER INFORMATION: Synthetic primer

<400> SEQUENCE: 193
agccgctcgc ctcacta            17

<210> SEQ ID NO 194
<211> LENGTH: 20
<212> TYPE: DNA
<213> ORGANISM: Artificial Sequence
<220> FEATURE:
<223> OTHER INFORMATION: Synthetic primer

<400> SEQUENCE: 194
acccggttgt tgttggtgaa            20

<210> SEQ ID NO 195
<211> LENGTH: 18
<212> TYPE: DNA

<213> ORGANISM: Artificial Sequence
<220> FEATURE:
<223> OTHER INFORMATION: Synthetic primer

<400> SEQUENCE: 195
ggcagcagtg accagaac                                                     18

<210> SEQ ID NO 196
<211> LENGTH: 19
<212> TYPE: DNA
<213> ORGANISM: Artificial Sequence
<220> FEATURE:
<223> OTHER INFORMATION: Synthetic primer

<400> SEQUENCE: 196
tgctgtggga gtcactgaa                                                    19

<210> SEQ ID NO 197
<211> LENGTH: 21
<212> TYPE: DNA
<213> ORGANISM: Artificial Sequence
<220> FEATURE:
<223> OTHER INFORMATION: Synthetic primer

<400> SEQUENCE: 197
gttggatggc aatcgaatca c                                                 21

<210> SEQ ID NO 198
<211> LENGTH: 22
<212> TYPE: DNA
<213> ORGANISM: Artificial Sequence
<220> FEATURE:
<223> OTHER INFORMATION: Synthetic primer

<400> SEQUENCE: 198
ccagagcaat acaccatagg ac                                                22

<210> SEQ ID NO 199
<211> LENGTH: 20
<212> TYPE: DNA
<213> ORGANISM: Artificial Sequence
<220> FEATURE:
<223> OTHER INFORMATION: Synthetic primer

<400> SEQUENCE: 199
actgaggaac tccgttgtca                                                   20

<210> SEQ ID NO 200
<211> LENGTH: 21
<212> TYPE: DNA
<213> ORGANISM: Artificial Sequence
<220> FEATURE:
<223> OTHER INFORMATION: Synthetic primer

<400> SEQUENCE: 200
aggaagtgca ggaagaagtc a                                                 21

<210> SEQ ID NO 201
<211> LENGTH: 20
<212> TYPE: DNA
<213> ORGANISM: Artificial Sequence
<220> FEATURE:
<223> OTHER INFORMATION: Synthetic primer

<400> SEQUENCE: 201
gctgcgcttg cagagattaa                                                   20

<210> SEQ ID NO 202
<211> LENGTH: 22
<212> TYPE: DNA
<213> ORGANISM: Artificial Sequence
<220> FEATURE:
<223> OTHER INFORMATION: Synthetic primer

<400> SEQUENCE: 202
gtaacgccag gaattgttgc ta                                             22

<210> SEQ ID NO 203
<211> LENGTH: 22
<212> TYPE: DNA
<213> ORGANISM: Artificial Sequence
<220> FEATURE:
<223> OTHER INFORMATION: Synthetic primer

<400> SEQUENCE: 203
gcgaatccca tgagctccaa ta                                             22

<210> SEQ ID NO 204
<211> LENGTH: 20
<212> TYPE: DNA
<213> ORGANISM: Artificial Sequence
<220> FEATURE:
<223> OTHER INFORMATION: Synthetic primer

<400> SEQUENCE: 204
cttatgccgc cacacttgac                                                20

<210> SEQ ID NO 205
<211> LENGTH: 20
<212> TYPE: DNA
<213> ORGANISM: Artificial Sequence
<220> FEATURE:
<223> OTHER INFORMATION: Synthetic primer

<400> SEQUENCE: 205
cgtcgctttg tcttcagcaa                                                20

<210> SEQ ID NO 206
<211> LENGTH: 19
<212> TYPE: DNA
<213> ORGANISM: Artificial Sequence
<220> FEATURE:
<223> OTHER INFORMATION: Synthetic primer

<400> SEQUENCE: 206
atcacgcagg catcttcca                                                 19

<210> SEQ ID NO 207
<211> LENGTH: 20
<212> TYPE: DNA
<213> ORGANISM: Artificial Sequence
<220> FEATURE:
<223> OTHER INFORMATION: Synthetic primer

<400> SEQUENCE: 207
cacagcgtgg tggtacctta                                                20

<210> SEQ ID NO 208
<211> LENGTH: 22
<212> TYPE: DNA
<213> ORGANISM: Artificial Sequence
<220> FEATURE:

<223> OTHER INFORMATION: Synthetic primer

<400> SEQUENCE: 208
cccatgcagg agctattaca ca                                    22

<210> SEQ ID NO 209
<211> LENGTH: 21
<212> TYPE: DNA
<213> ORGANISM: Artificial Sequence
<220> FEATURE:
<223> OTHER INFORMATION: Synthetic primer

<400> SEQUENCE: 209
cccaaacaga ggcagagtgt a                                     21

<210> SEQ ID NO 210
<211> LENGTH: 20
<212> TYPE: DNA
<213> ORGANISM: Artificial Sequence
<220> FEATURE:
<223> OTHER INFORMATION: Synthetic primer

<400> SEQUENCE: 210
tgacccagat ggtggtttcc                                       20

<210> SEQ ID NO 211
<211> LENGTH: 21
<212> TYPE: DNA
<213> ORGANISM: Artificial Sequence
<220> FEATURE:
<223> OTHER INFORMATION: Synthetic primer

<400> SEQUENCE: 211
ccagcacata ggagagatga g                                     21

<210> SEQ ID NO 212
<211> LENGTH: 22
<212> TYPE: DNA
<213> ORGANISM: Artificial Sequence
<220> FEATURE:
<223> OTHER INFORMATION: Synthetic primer

<400> SEQUENCE: 212
ctggctttgt tctgtctttc tt                                    22

<210> SEQ ID NO 213
<211> LENGTH: 21
<212> TYPE: DNA
<213> ORGANISM: Artificial Sequence
<220> FEATURE:
<223> OTHER INFORMATION: Synthetic primer

<400> SEQUENCE: 213
gatttctctg cctctgccaa c                                     21

<210> SEQ ID NO 214
<211> LENGTH: 21
<212> TYPE: DNA
<213> ORGANISM: Artificial Sequence
<220> FEATURE:
<223> OTHER INFORMATION: Synthetic primer

<400> SEQUENCE: 214
caaccagagg aagtgactcc a                                     21

```
<210> SEQ ID NO 215
<211> LENGTH: 20
<212> TYPE: DNA
<213> ORGANISM: Artificial Sequence
<220> FEATURE:
<223> OTHER INFORMATION: Synthetic primer

<400> SEQUENCE: 215
agtttggtgg acctcatgca                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic primer

<400> SEQUENCE: 216
gttacatagc gcacggcaaa                                              20

<210> SEQ ID NO 217
<211> LENGTH: 21
<212> TYPE: DNA
<213> ORGANISM: Artificial Sequence
<220> FEATURE:
<223> OTHER INFORMATION: Synthetic primer

<400> SEQUENCE: 217
tccttcgccc aggttgttat a                                            21

<210> SEQ ID NO 218
<211> LENGTH: 19
<212> TYPE: DNA
<213> ORGANISM: Artificial Sequence
<220> FEATURE:
<223> OTHER INFORMATION: Synthetic primer

<400> SEQUENCE: 218
cagagaggct gtgcaccta                                               19

<210> SEQ ID NO 219
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 219
gatcggaaga gcacacgtct                                              20

<210> SEQ ID NO 220
<211> LENGTH: 33
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (33)..(33)
<223> OTHER INFORMATION: Phosphorothioate

<400> SEQUENCE: 220
acactctttc cctacacgac gctcttccga tct                               33

<210> SEQ ID NO 221
<211> LENGTH: 58
<212> TYPE: DNA
```

```
<213> ORGANISM: Artificial Sequence
<220> FEATURE:
<223> OTHER INFORMATION: Synthetic primer

<400> SEQUENCE: 221
aatgatacgg cgaccaccga gatctacact ctttccctac acgacgctct tccgatct        58

<210> SEQ ID NO 222
<211> LENGTH: 64
<212> TYPE: DNA
<213> ORGANISM: Artificial Sequence
<220> FEATURE:
<223> OTHER INFORMATION: Synthetic primer

<400> SEQUENCE: 222
caagcagaag acggcatacg agatcgtgat gtgactggag ttcagacgtg tgctcttccg        60
atct                                                                    64

<210> SEQ ID NO 223
<211> LENGTH: 64
<212> TYPE: DNA
<213> ORGANISM: Artificial Sequence
<220> FEATURE:
<223> OTHER INFORMATION: Synthetic primer

<400> SEQUENCE: 223
caagcagaag acggcatacg agatacatcg gtgactggag ttcagacgtg tgctcttccg        60
atct                                                                    64

<210> SEQ ID NO 224
<211> LENGTH: 64
<212> TYPE: DNA
<213> ORGANISM: Artificial Sequence
<220> FEATURE:
<223> OTHER INFORMATION: Synthetic primer

<400> SEQUENCE: 224
caagcagaag acggcatacg agatgcctaa gtgactggag ttcagacgtg tgctcttccg        60
atct                                                                    64

<210> SEQ ID NO 225
<211> LENGTH: 64
<212> TYPE: DNA
<213> ORGANISM: Artificial Sequence
<220> FEATURE:
<223> OTHER INFORMATION: Synthetic primer

<400> SEQUENCE: 225
caagcagaag acggcatacg agattggtca gtgactggag ttcagacgtg tgctcttccg        60
atct                                                                    64

<210> SEQ ID NO 226
<211> LENGTH: 64
<212> TYPE: DNA
<213> ORGANISM: Artificial Sequence
<220> FEATURE:
<223> OTHER INFORMATION: Synthetic primer

<400> SEQUENCE: 226
caagcagaag acggcatacg agatcactgt gtgactggag ttcagacgtg tgctcttccg        60
atct                                                                    64
```

```
<210> SEQ ID NO 227
<211> LENGTH: 64
<212> TYPE: DNA
<213> ORGANISM: Artificial Sequence
<220> FEATURE:
<223> OTHER INFORMATION: Synthetic primer

<400> SEQUENCE: 227
caagcagaag acggcatacg agatattggc gtgactggag ttcagacgtg tgctcttccg      60
atct                                                                  64

<210> SEQ ID NO 228
<211> LENGTH: 64
<212> TYPE: DNA
<213> ORGANISM: Artificial Sequence
<220> FEATURE:
<223> OTHER INFORMATION: Synthetic primer

<400> SEQUENCE: 228
caagcagaag acggcatacg agatgatctg gtgactggag ttcagacgtg tgctcttccg      60
atct                                                                  64

<210> SEQ ID NO 229
<211> LENGTH: 64
<212> TYPE: DNA
<213> ORGANISM: Artificial Sequence
<220> FEATURE:
<223> OTHER INFORMATION: Synthetic primer

<400> SEQUENCE: 229
caagcagaag acggcatacg agattcaagt gtgactggag ttcagacgtg tgctcttccg      60
atct                                                                  64
```